US009238834B2

(12) United States Patent
Drmanac et al.

(10) Patent No.: US 9,238,834 B2
(45) Date of Patent: Jan. 19, 2016

(54) EFFICIENT SHOTGUN SEQUENCING METHODS

(71) Applicant: Complete Genomics, Inc., Mountain View, CA (US)

(72) Inventors: Radoje T. Drmanac, Los Altos Hills, CA (US); Clifford Reid, Pacifica, CA (US)

(73) Assignee: Complete Genomics, Inc., Mountain View, CA (US)

( * ) Notice: Subject to any disclaimer, the term of this patent is extended or adjusted under 35 U.S.C. 154(b) by 266 days.

(21) Appl. No.: 13/647,338

(22) Filed: Oct. 8, 2012

(65) Prior Publication Data

US 2013/0059737 A1 Mar. 7, 2013

Related U.S. Application Data

(63) Continuation of application No. 12/325,922, filed on Dec. 1, 2008, now Pat. No. 8,298,768.

(60) Provisional application No. 61/116,193, filed on Nov. 19, 2008, provisional application No. 60/991,605, filed on Nov. 30, 2007, provisional application No. 60/991,141, filed on Nov. 29, 2007.

(51) Int. Cl.
*C12P 19/34* (2006.01)
*C12Q 1/68* (2006.01)

(52) U.S. Cl.
CPC ............ *C12Q 1/6869* (2013.01); *C12Q 1/6874* (2013.01)

(58) Field of Classification Search
USPC .................................... 435/6.12, 91.2, 91.52
See application file for complete search history.

(56) References Cited

U.S. PATENT DOCUMENTS

| | | |
|---|---|---|
| 4,719,179 A | 1/1988 | Baranay |
| 4,883,750 A | 11/1989 | Whiteley |
| 5,091,302 A | 2/1992 | Newman |
| 5,124,246 A | 6/1992 | Urdea |
| 5,143,854 A | 9/1992 | Pirrung |
| 5,202,231 A | 4/1993 | Drmanac |
| 5,354,668 A | 10/1994 | Auerbach |
| 5,403,708 A | 4/1995 | Brennan |
| 5,426,180 A | 6/1995 | Kool |
| 5,427,930 A | 6/1995 | Birkenmeyer |
| 5,474,796 A | 12/1995 | Brennan |
| 5,508,169 A | 4/1996 | Deugau |
| 5,525,464 A | 6/1996 | Drmanac |
| 5,632,957 A | 5/1997 | Heller |
| 5,641,658 A | 6/1997 | Adams |
| 5,648,245 A | 7/1997 | Fire |
| 5,710,000 A | 1/1998 | Sapolsky |
| 5,714,320 A | 2/1998 | Kool |
| 5,728,524 A | 3/1998 | Sibson |
| 5,744,305 A | 4/1998 | Fodor |
| 5,800,992 A | 9/1998 | Fodor |
| 5,854,033 A | 12/1998 | Lizardi |
| 5,866,337 A | 2/1999 | Schon |
| 5,871,921 A | 2/1999 | Landegren |
| 5,888,737 A | 3/1999 | DuBridge |
| 5,994,068 A | 11/1999 | Guilfoyle |
| 6,004,755 A | 12/1999 | Wang |
| 6,013,445 A | 1/2000 | Albrecht |
| 6,045,994 A | 4/2000 | Zabeau |
| 6,077,668 A | 6/2000 | Kool |
| 6,096,880 A | 8/2000 | Kool |
| 6,124,120 A | 9/2000 | Lizardi |
| 6,136,537 A | 10/2000 | Macevicz |
| 6,143,495 A | 11/2000 | Lizardi |
| 6,143,527 A | 11/2000 | Pachuk |
| 6,210,891 B1 | 4/2001 | Nyren |
| 6,210,894 B1 | 4/2001 | Brennan |
| 6,218,152 B1 | 4/2001 | Auerbach |
| 6,221,603 B1 | 4/2001 | Mahtani |
| 6,255,469 B1 | 7/2001 | Seeman |
| 6,258,539 B1 | 7/2001 | Hunkapillar |
| 6,261,808 B1 | 7/2001 | Auerbach |
| 6,270,961 B1 | 8/2001 | Drmanac |

(Continued)

FOREIGN PATENT DOCUMENTS

| | | |
|---|---|---|
| JP | 4-262799 | 9/1992 |
| JP | 4-304900 | 10/1992 |
| WO | 95/09248 | 4/1995 |
| WO | 01/62982 | 8/2001 |
| WO | 02/074988 | 9/2002 |
| WO | 03/012119 | 2/2003 |
| WO | 2004/072294 | 8/2004 |
| WO | 2004/076683 | 9/2004 |
| WO | 2005/040425 | 5/2005 |
| WO | 2005/047523 | 5/2005 |

(Continued)

OTHER PUBLICATIONS

Bankier, "Shotgun DNA Sequencing," Methods in Mol. Biol., V. 167, p. 89-100, (2001).

(Continued)

*Primary Examiner* — Kenneth R. Horlick
*Assistant Examiner* — Joyce Tung
(74) *Attorney, Agent, or Firm* — Kilpatrick Townsend & Stockton LLP

(57) ABSTRACT

Methods are provided for efficient shotgun sequencing to allow efficient selection and sequencing of nucleic acids of interest contained in a library. The nucleic acids of interest can be defined any time before or after preparation of the library. One example of nucleic acids of interest is missing or low confidence genome sequences resulting from an initial sequencing procedure. Other nucleic acids of interest include subsets of genomic DNA, RNA or cDNAs (exons, genes, gene sets, transciptomes). By designing an efficient (simple to implement, speedy, high specificity, low cost) selection procedure, a more complete sequence is achieved with less effort than by using highly redundant shotgun sequencing in an initial sequencing procedure.

25 Claims, 9 Drawing Sheets

(56) References Cited

U.S. PATENT DOCUMENTS

| | | |
|---|---|---|
| 6,274,320 B1 | 8/2001 | Rothberg |
| 6,274,351 B1 | 8/2001 | Peponnet |
| 6,284,497 B1 | 9/2001 | Sabanayagam |
| 6,287,824 B1 | 9/2001 | Lizardi |
| 6,291,183 B1 | 9/2001 | Pirrung |
| 6,297,006 B1 | 10/2001 | Drmanac |
| 6,297,016 B1 | 10/2001 | Egholm |
| 6,306,597 B1 | 10/2001 | Macevicz |
| 6,309,824 B1 | 10/2001 | Drmanac |
| 6,316,229 B1 | 11/2001 | Lizardi |
| 6,329,150 B1 | 12/2001 | Lizardi |
| 6,344,329 B1 | 2/2002 | Lizardi |
| 6,346,413 B1 | 2/2002 | Fodor |
| 6,355,432 B1 | 3/2002 | Fodor |
| 6,401,267 B1 | 6/2002 | Drmanac |
| 6,403,320 B1 | 6/2002 | Read |
| 6,413,722 B1 | 7/2002 | Arnold |
| 6,432,360 B1 | 8/2002 | Church |
| 6,472,156 B1 | 10/2002 | Wittwer |
| 6,491,871 B1 | 12/2002 | Fodor |
| 6,500,620 B2 | 12/2002 | Yu |
| 6,514,768 B1 | 2/2003 | Guire |
| 6,534,293 B1 | 3/2003 | Baranay |
| 6,558,928 B1 | 5/2003 | Landegren |
| 6,573,369 B2 | 6/2003 | Henderson |
| 6,576,448 B2 | 6/2003 | Weissman |
| 6,589,726 B1 | 7/2003 | Butler |
| 6,610,481 B2 | 8/2003 | Koch |
| 6,620,584 B1 | 9/2003 | Chee |
| 6,632,609 B2 | 10/2003 | Lizardi |
| 6,653,077 B1 | 11/2003 | Brenner |
| 6,783,943 B2 | 8/2004 | Christian |
| 6,787,308 B2 | 9/2004 | Balasubramanian |
| 6,812,005 B2 | 11/2004 | Fan |
| 6,828,100 B1 | 12/2004 | Ronaghi |
| 6,833,246 B2 | 12/2004 | Balasubramanian |
| 6,864,052 B1 | 3/2005 | Drmanac |
| 6,890,741 B2 | 5/2005 | Fan |
| 6,913,884 B2 | 7/2005 | Stuelpnagel |
| 6,977,153 B2 | 12/2005 | Kumar |
| 6,998,228 B2 | 2/2006 | Henderson |
| 7,011,945 B2 | 3/2006 | Qiao |
| 7,064,197 B1 | 6/2006 | Rabbani |
| 7,244,559 B2 | 7/2007 | Rothberg |
| 7,264,929 B2 | 9/2007 | Rothberg |
| 7,276,720 B2 | 10/2007 | Ulmer |
| 7,384,737 B2 | 6/2008 | Barnes |
| 7,544,473 B2 | 6/2009 | Brenner |
| 8,298,768 B2 * | 10/2012 | Drmanac et al. ............. 435/6.12 |
| 2002/0004204 A1 | 1/2002 | O'Keefe |
| 2002/0055100 A1 | 5/2002 | Kawashima |
| 2002/0076716 A1 | 6/2002 | Sabanayagam |
| 2002/0197621 A1 | 12/2002 | Drmanac |
| 2003/0068629 A1 | 4/2003 | Rothberg |
| 2003/0200033 A1 | 10/2003 | Segal et al. |
| 2004/0002090 A1 | 1/2004 | Mayer |
| 2004/0203061 A1 | 10/2004 | Barany et al. |
| 2004/0229221 A1 | 11/2004 | Schon |
| 2004/0248144 A1 | 12/2004 | Mir |
| 2004/0248161 A1 | 12/2004 | Rothberg |
| 2005/0019776 A1 | 1/2005 | Callow |
| 2005/0037356 A1 | 2/2005 | Gullberg |
| 2005/0042649 A1 | 2/2005 | Balasubramanian |
| 2005/0100939 A1 | 5/2005 | Namsaraev |
| 2005/0112639 A1 | 5/2005 | Wang et al. |
| 2005/0149272 A1 | 7/2005 | Pe' Er et al. |
| 2005/0176007 A1 | 8/2005 | De Leeuw et al. |
| 2005/0191656 A1 | 9/2005 | Drmanac |
| 2005/0214840 A1 | 9/2005 | Chen |
| 2005/0244863 A1 | 11/2005 | Mir |
| 2006/0012793 A1 | 1/2006 | Harris |
| 2006/0019276 A1 | 1/2006 | Harris |
| 2006/0024681 A1 | 2/2006 | Smith |
| 2006/0024711 A1 | 2/2006 | Lapidus |
| 2006/0223097 A1 | 10/2006 | Sapolsky |
| 2007/0015182 A1 | 1/2007 | Abarzua |
| 2007/0037152 A1 | 2/2007 | Drmanac |
| 2007/0037197 A1 | 2/2007 | Young |
| 2007/0072208 A1 | 3/2007 | Drmanac |
| 2007/0099208 A1 | 5/2007 | Drmanac |
| 2007/0141604 A1 | 6/2007 | Gormley et al. |
| 2008/0234136 A1 | 9/2008 | Drmanac |
| 2008/0318796 A1 | 12/2008 | Drmanac |
| 2009/0005252 A1 | 1/2009 | Drmanac |
| 2009/0005259 A1 | 1/2009 | Drmanac |
| 2009/0011416 A1 | 1/2009 | Drmanac |
| 2009/0011943 A1 | 1/2009 | Drmanac |
| 2009/0036316 A1 | 2/2009 | Drmanac |
| 2009/0099041 A1 | 4/2009 | Church |
| 2009/0118488 A1 | 5/2009 | Drmanac |
| 2009/0137404 A1 | 5/2009 | Drmanac |
| 2009/0137414 A1 | 5/2009 | Drmanac |
| 2009/0155781 A1 | 6/2009 | Drmanac |
| 2009/0264299 A1 | 10/2009 | Drmanac |
| 2009/0305248 A1 | 12/2009 | Lander et al. |

FOREIGN PATENT DOCUMENTS

| | | |
|---|---|---|
| WO | 2005/078130 | 8/2005 |
| WO | 2005/080605 | 9/2005 |
| WO | 2005/082098 | 9/2005 |
| WO | 2005/093094 | 10/2005 |
| WO | 2005/116262 | 12/2005 |
| WO | 2006/007207 | 1/2006 |
| WO | 2006/040549 | 4/2006 |
| WO | 2006/055521 | 5/2006 |
| WO | 2006/073504 | 7/2006 |
| WO | 2006/084132 | 8/2006 |
| WO | 2006/138257 | 12/2006 |
| WO | 2007/014397 | 2/2007 |
| WO | 2007/025124 | 3/2007 |
| WO | 2007/061425 | 5/2007 |
| WO | 2007/062160 | 5/2007 |
| WO | 2007/106509 | 9/2007 |
| WO | 2007/120208 | 10/2007 |
| WO | 2007/121489 | 10/2007 |

OTHER PUBLICATIONS

Batzoglou et al, "Arachne: A whole-genome shotgun assembler," Genome Research, 12: 177-189 (2002).

Blanco et al., "Highly efficient DNA synthesis by the phage phi 29 DNA polymerase," J. Biol. Chem., v. 264, issue 15, p. 8935-8940 (1989).

Brenner et al, "Gene Expression Analysis by Massivly Parallel Signature Sequencing (MPSS) on Microbead Arrays," Nature Biotechnology, v. 18, p. 630-634 (2000).

Callow, Matthew J., et al. "Selective DNA amplification from complex genomes using universal double-sided adapters," Nucleic Acids Research, vol. 32, No. 2, e21, p. 1-6, (Jan. 2004).

Chen et al., "A Homogeneous, Ligase-Mediated DNA Diagnostic Test", Genome Research, vol. 8, No. 5, May 1998, pp. 549-556.

Collins et al, "Directional cloning of DNA fragments at a large distance from an initial probe: A circularization method," Proc. Natl. Acad. Sci., 81: 6812-6816 (1984). cited by other.

Cowie et al, "Identification of APC gene mutations in colorectal cancer using universal microarray-based combinatorial sequencing-by-hybridization," Human Mutation, 24:261-271 (2004).

Dahl et al, "Multiplex amplification enabled by selective circularization of large sets of genomic DNA fragments," Nucleic Acids Research, 33(8): e71 (2005).

Havlak et al, "The Atlas genome assembly system," Genome Research, 14: 721-732 (2004).

Ladner, D.P. et al., "Multiplex detection of hotspot mutations by rolling circl-enabled universal microarrays," Laboratory Investigation, US and CA Academy of Pathology, vol. 81, No. 8, p. 1079-1086 (Aug. 1, 2001).

Li, M. et al., "BEAMing up for detection and quantification of rare sequence variants," Nature Methods, vol. 3, pp. 95-97 (2006).

Li, P. et al., "PRIMO: A primer design program that applies base quality statistics for automated large-scale DNA sequencing," Genomics, Academic Press, V. 40, No. 3, p. 476-485, (1997).

(56) References Cited

OTHER PUBLICATIONS

Metzker, "Emerging Technologies in DNA Sequencing," Genome Research, 15: 1767-1776 (2005).

Mullikin et al., "The Phusion Assembler," Genome Research, 13:81-90(2003).

Okou, David T. et al., "Microarray-based genomic selection for high-throughput resequencing," Nature Methods, V. 4, No. 11, p. 907-909, (2007).

Pevzner et al, "An Eulerian path approach to DNA fragment assembly," Proc. Natl. Acad. Sci., 98: 9748-9753 (2001).

Shendure et al, "Accurate multiplex polony sequencing of an evolved bacterial genome," Science, 309: 1728-1732 (2005).

Shendure et al, "Advanced Sequencing Technologies: Methods and Goals," Nature Reviews Genetics, vol. 5, pp. 335-344 (2004).

Smirnov et al, "Method of manufacturing whole-genome microarrays by rolling circle amplification," Genes, Chromosomes & Cancer, 40: 72-77 (2004).

Tringe et al, "Metagenomics: DNA Sequencing of Environmental Samples," Nature Reviews Genetics, vol. 6, pp. 805-814 (2005. cited by other.

Vingron et al., "Sequence Alignment and Penalty Choice Review of Concepts, Case Studies and Implications," J. Mol. Biol, vol. 235, issue 1, pp. 1-12 (1994).

Voss, H. et al., "Efficient Low Redundancy Large-Scale DNA Sequencing at EMBL," J. Biotechn., v. 41, No. 2, (1995).

\* cited by examiner

Fig. 1 100 →

...bbbbbbbbbbbbbbbbbbbbbbbGbbbbbbbbbbbbbbbbbbbbbbb...
⎫
⎬ 902

HO-BBBBBBBBBBBBBBBBBBBB-OH
⎫
⎬ 904

P-CNNNNNNNN-Biotin
⎫
⎬ 906

⌐902
...bbbbbbbbbbbbbbbbbbbbbbbGbbbbbbbbbbbbbbbbbbbbbbb...
BBBBBBBBBBBBBBBBBBBBBCNNNNNNNN⏋
⎬          OH P   ⎬       ⎬ 908
904              906    Biotin ⌐902
...bbbbbbbbbbbbbbbbbbbbbbbGbbbbbbbbbbbbbbbbbbbbbbb...
BBBBBBBBBBBBBBBBBBBBBCNNNNNNNN⏋
⎬                 ⎬   ⎬       ⎬ 910
904              912  906    Biotin

Fig. 9

EFFICIENT SHOTGUN SEQUENCING METHODS

The present application is a continuation of Ser. No. 12/325,922, filed Dec. 1, 2008 (pending), which claims the benefit of 61/116,193, filed Nov. 19, 2008; 60/991,605, filed Nov. 30, 2007; and 60/991,141, filed Nov. 29, 2007. Application Ser. No. 12/325,922 is hereby incorporated by reference in its entirety for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 92171-854301_ST25.TXT, created on Nov. 7, 2012, 1,051 bytes, machine format IBM-PC, MS-Windows operating system, is hereby incorporated by reference.

BACKGROUND

Large-scale sequence analysis of genomic DNA is central to understanding a wide range of biological phenomena related to health and disease in humans and in economically important plants and animals. The need for low-cost, high-throughput sequencing and re-sequencing has led to the development of new approaches to sequencing that employ parallel analysis of many target DNA fragments simultaneously. Improvements to sequencing methods and increasing the amount and quality of data from such methods is of great value in the art.

SUMMARY

Embodiments described and claimed herein address the foregoing and other situations by providing two-, three- or more multi-phased methods for efficient shotgun sequencing or sequencing of complex target nucleic acids allowing thorough and rapid selection and re-sequencing of sequences of interest contained in a library. The nucleic acids of interest can be defined before or after preparation of the library or other sample of nucleic acids. One example of sequences of interest are genome sequences with missing or low confidence base calls resulting from an initial sequencing procedure. Other sequences of interest include sequence differences that are identified by comparison to a reference sequence. Other sequences of interest include subsets of genomic DNA, RNA or cDNAs (exons, genes, gene sets, transcriptomes). By designing efficient, easily-implemented, high specificity and low cost selection and re-sequencing procedures, a more complete sequence is achieved than by using highly redundant shotgun sequencing in an initial sequencing procedure (e.g., coverage of up to 100× genome equivalents or more).

According one embodiment of the invention, methods of sequencing a target nucleic acid are provided, such methods comprising: (a) sequencing the target nucleic acid to produce a primary target nucleic acid sequence that comprises one or more sequences of interest; (b) synthesizing a plurality of target-specific oligonucleotides, wherein each of said plurality of target-specific oligonucleotides corresponds to at least one of the sequences of interest; (c) providing a library of fragments of the target nucleic acid (or constructs that comprise such fragments and that may further comprise, for example, adaptors and other sequences as described below) that hybridize to the plurality of target-specific oligonucleotides; and (d) sequencing the library of fragments (or constructs that comprise such fragments) to produce a secondary target nucleic acid sequence. The target nucleic acid may be any nucleic acid, including but not limited to genomic DNA from any organism, such as, for example, genomes of organisms such as bacteria, fungi (e.g., yeast), amphibians, reptiles, birds, and mammals, e.g., humans. In order to close gaps due to missing sequence or resolve low confidence base calls in a primary sequence of genomic DNA, such as human genomic DNA, the number of target-specific oligonucleotides that are synthesized for these methods may be from about ten thousand to about one million; thus the present invention contemplates the use of at least about 10,000 target-specific oligonucleotides, or about 25,000, or about 50,000, or about 100,000, or about 20,000, or about 50,000, or about 100,000, or about 200,000 or more.

In saying that the plurality of target-specific oligonucleotides "corresponds to" at least one of the sequences of interest, it is meant that such target-specific oligonucleotides are designed to hybridize to the target nucleic acid in proximity to, including but not limited to, adjacent to, the sequence of interest such that there is a high likelihood that a fragment of the target nucleic acid that hybridizes to such an oligonucleotides will include the sequence of interest. Such target-specific oligonucleotides are therefore useful for hybrid capture methods to produce a library of fragments enriched for such sequences of interest, as sequencing primers for sequencing the sequence of interest, as amplification primers for amplifying the sequence of interest, or for other purposes.

The sequencing methods of the present invention are well suited to use in sequencing shotgun libraries of fragments of a complex target nucleic acid. Accordingly, in such methods sequencing the target nucleic acid may comprise sequencing a first shotgun library of fragments of the target nucleic acid that represents a majority of sequences of the target nucleic acid. According to another embodiment, such a method may comprise hybridizing the plurality of oligonucleotides to a second shotgun library of fragments of the target nucleic acid, which may, for example, constitute an aliquot of the first shotgun library or a different library prepared in a similar or different fashion from the first library.

In another embodiment, the plurality of target-specific oligonucleotides is hybridized as a pool to the library of fragments.

In order to prepare the library of fragments of the target nucleic acid that hybridize to the plurality of target-specific oligonucleotides, such methods may comprise providing a plurality of constructs that each comprise a fragment of the target nucleic acid and separating constructs that hybridize to the plurality of target-specific oligonucleotides from constructs that do not hybridize to the plurality of target-specific oligonucleotides, thereby producing the library (i.e., hybrid capture). For example, the plurality of oligonucleotides can be attached to a solid support, i.e., the plurality of target-specific oligonucleotides can be attached to a single solid support or to a plurality of solid supports (e.g., each oligonucleotides attached to a different solid support), such as beads, as is described herein. After hybridization of the library of fragments of the target nucleic acid to the target-specific oligonucleotides bound to solid support(s), non-hybridized fragments can readily be eliminated, e.g., by washing. As one alternative approach, each of the target-specific oligonucleotides may comprise a binding moiety for attachment of each of said plurality of oligonucleotides to a solid support. In this approach, after hybridizing constructs that each comprise a fragment of the target nucleic acid to the target-specific oligonucleotides, the target-specific oligonucleotides (and thus constructs hybridized to such target-specific oligonucleotides) can be attached to a solid support for separation away from non-hybridized constructs. Such a binding moiety may for example, be biotin or any other known member of a binding pair such as antigen/antibody, hapten-antibody, lectin/carbohydrate, apoprotein/cofactor, etc.

In another embodiment, such methods may comprise amplifying the library of constructs, thereby producing an amplified enriched library of constructs, then sequencing the amplified enriched library of constructs. The library of constructs may be amplified by any known nucleic acid amplification method, including, for example, circle-dependent amplification. In one embodiment, the target-specific oligonucleotides serve as primers for such circle-dependent amplification.

In one embodiment of such methods, the library of constructs comprises from about 0.1 percent to about 10 percent of sequence of the target nucleic acid. As is explained herein, enriching for constructs comprising fragments that include sequences of interest allows the sequence redundancy for the primary sequence [commonly 5-fold (5×) to 50-fold (50×)] redundancy or coverage to be substantially lower than for the enriched library of constructs. Stated differently, by focusing the secondary sequencing effort on a small fraction of the target nucleic acid sequences, the redundancy of the secondary sequencing effort can be high enough (for example, 100-fold [100×]) to substantially improve the overall redundancy of the sequence produced by combining the results of the primary and secondary sequencing efforts. Thus, according to one embodiment, secondary target nucleic acid sequence has a substantially higher redundancy than the primary target nucleic acid sequence, for example two-fold, three-fold, four-fold, five-fold, six-fold, seven-fold, eight-fold, nine-fold, or ten-fold or more higher. It should be noted that redundancy (or coverage) as used herein is an average figure; in an ideal case of shotgun sequencing, a 20× redundancy is not uniform across all sequences of a target genome but is actually a Poisson distribution ranging from about 0-200×. Therefore, it is highly advantageous to perform a first sequencing run at 5× to 20×, for example, with one or more substantially higher redundancy sequencing runs focusing on small fractions of the target genome, resulting in a final sequence that has a substantially higher overall redundancy with much lower effort and cost.

In shotgun sequencing and other sequencing methods according to the present invention, after assembly of sequencing reads, to the skilled person it is apparent from the assembled sequence that gaps exist or that there is low confidence in one or more bases or stretches of bases at a particular site in the sequence. Sequences of interest, which may include such gaps, low confidence sequence, or simply different sequences at a particular location (i.e., a change of one or more nucleotides in target sequence), can also be identified by comparing the primary target nucleic acid sequence to a reference sequence.

According to another embodiment of such methods sequencing the target nucleic acid to produce a primary target nucleic acid sequence comprises computerized input of sequence readings and computerized assembly of the sequence readings to produce the primary target nucleic acid sequence. In addition, design of the target-specific oligonucleotides can be computerized, and such computerized synthesis of the target-specific oligonucleotides can be integrated with the computerized input and assembly of the sequence readings and design of the target-specific oligonucleotides. This is especially helpful since the number of target-specific oligonucleotides to be synthesized can be in the tens of thousands or hundreds of thousands for genomes of higher organisms such as humans, for example. Thus the invention provides automated integration of the process of creating the oligonucleotide pool from the determined sequences and the regions identified for further processing. Preferably, a computer-driven program uses the identified regions and determined sequence near or adjacent to such identified regions to design oligonucleotides to isolate and/or create new fragments that cover these regions. The oligonucleotides can then be used as described herein to isolate fragments, either from the first sequencing library, from a precursor of the first sequencing library, from a different sequencing library created from the same target nucleic acid, directly from target nucleic acids, and the like. Preferably, this automated integration of identifying regions for further analysis and isolating/creating the second library defines the sequence of the oligonucleotides within the oligonucleotide pool and directs synthesis of these oligonucleotides.

According to another embodiment of the invention, methods are provided for sequencing genomic DNA comprising: (a) sequencing a first shotgun library of fragments of the genomic DNA to produce a primary genomic sequence that comprises one or more sequences of interest; (b) synthesizing a plurality of oligonucleotides, wherein each of said plurality of oligonucleotides corresponds to at least one of said sequences of interest; (c) hybridizing a pool of said plurality of oligonucleotides to a second shotgun library of fragments of the genomic DNA; (d) preparing an enriched library of fragments of said genomic DNA from the second shotgun library that hybridize to the pool of said plurality of oligonucleotides; and sequencing the enriched shotgun library to produce a secondary target nucleic acid sequence.

In some aspects of the technology, a releasing process is performed after the hybrid capture process, and in other aspects of the technology, an amplification process is performed before the second sequencing process.

According to another embodiment of the invention, methods are provided for sequencing a target nucleic acid comprising: (a) sequencing the target nucleic acid to produce a primary target nucleic acid sequence that comprises one or more sequences of interest; (b) synthesizing a plurality of target-specific oligonucleotides, wherein each of said plurality of oligonucleotides corresponds to at least one of said sequences of interest; (c) providing a library of fragments of the target nucleic acid; (d) hybridizing said plurality of target-specific oligonucleotides to the library of fragments of the target nucleic acid; (e) hybridizing universal oligonucleotides to the library of fragments of the target nucleic acid; (f) ligating the universal oligonucleotides to adjacently hybridized target specific oligonucleotides, thereby producing universal oligonucleotide:target-specific oligonucleotide hybrids; (g) preparing an enriched library of fragments of the target nucleic acid by capturing fragments of the target nucleic acid that are hybridized to the universal oligonucleotide:target-specific oligonucleotide hybrids; and (h) sequencing the enriched library to produce a secondary target nucleic acid sequence. In some aspects of the technology, the universal oligonucleotides comprise a formula 5'-P-BxNy-Tag-3', where the 5' end is phosphorylated, B denotes specific bases, x is about 1 to about 5, N denotes degenerate or universal, y is about 5 to about 15, preferably about 6 to about 12, and a capture tag such as biotin is at the 3' end.

According to another embodiment of the invention, methods are provided for sequencing a target nucleic acid comprising: (a) sequencing the target nucleic acid to produce a primary target nucleic acid sequence that comprises one or more sequences of interest; (b) synthesizing a plurality of target-specific oligonucleotides, wherein each of said plurality of oligonucleotides corresponds to at least one of said sequences of interest; (d) providing a library of constructs, each construct comprising a fragment of the target nucleic acid; (e) hybridizing said plurality of oligonucleotides to the library of constructs; (f) amplifying the library of constructs using said plurality of oligonucleotides as primers, thereby producing an amplified library; and (g) sequencing the amplified library to produce a secondary target nucleic acid sequence.

It will be appreciated by the skilled person that the above-described methods are iterative. That is, in order to close gaps, resolve low confidence base calls and confirm the sequence at particular locations, for example, the process may be repeated. It will also be appreciated that any of the steps of the above-described methods may be automated.

In various aspects of these methods, the second shotgun sequencing library is isolated from the first shotgun sequencing library, and in other aspects, the second shotgun sequencing library is isolated from precursors of the first shotgun sequencing library. In yet other aspects, the second shotgun sequencing library is isolated from a different shotgun sequencing library comprising fragments of the complex target nucleic acid. In yet other aspects, the second shotgun sequencing library is isolated using a pool of oligonucleotides comprising sequences complementary to a sequence or a portion of a sequence from region's identified in the identifying process, and in some aspects, the oligonucleotides are complementary to a sequence or a portion of a sequence from regions adjacent to the regions identified in the identifying process.

In yet other aspects, some or all regions are identified in the identifying step by comparison of determined sequences with a reference sequence. In some aspects, the second shotgun sequencing library is isolated using a pool of oligonucleotides comprising oligonucleotides based on a reference sequence. Also, in some aspects, the pool of oligonucleotides comprises at least 1000 oligonucleotides of different sequence, in other aspects, the pool of oligonucleotides comprises at least 10,000, 25,000, 50,000, 75,000, or 100,000 or more oligonucleotides of different sequence.

In some aspects of the technology, one or more of the sequencing processes is performed by sequencing-by-ligation, and in other aspects, one or more of the sequencing processes is performed by sequencing-by-hybridization or sequencing-by-synthesis.

In certain aspects of the technology, between about 1 to about 30% of the complex target nucleic acid is identified as having to be re-sequenced in Phase II of the methods, and in other aspects, between about 1 to about 10% of the complex target nucleic acid is identified as having to be re-sequenced in Phase II of the methods. In some aspects, coverage for the identified percentage of complex target nucleic acid is between about 25× to about 100×.

In aspects of the technology, 1 to about 10 target-specific selection oligonucleotides are defined and synthesized for each target nucleic acid region that is re-sequenced in Phase II of the methods; in other aspects, about 3 to about 6 target-specific selection oligonucleotides are defined for each target nucleic acid region that is re-sequenced in Phase II of the methods.

In aspects of the technology, the target-specific selection oligonucleotides are identified and synthesized by an automated process, wherein the process that identifies regions of the complex nucleic acid missing nucleic acid sequence or having low confidence nucleic acid sequence and defines sequences for the target-specific selection oligonucleotides communicates with oligonucleotide synthesis software and hardware to synthesize the target-specific selection oligonucleotides. In other aspects of the technology, the target-specific selection oligonucleotides are between about 20 and about 30 bases in length, and in some aspects are unmodified.

In some aspects of the technology, the target nucleic acid is genomic DNA; in other aspects of the technology, the target nucleic acid is cDNA, RNA or pre-defined nucleic acids known to be related to, e.g., a disease or other condition. In various aspects of the technology, the library constructs comprise stretches of target nucleic acid from about 12 to about 24 bases in length between adaptors that are about 20 to about 50 bases in length. In other aspects, the library constructs further include a stretch of target nucleic acid of about 200 to about 10,000 bases.

Not all regions identified for further analysis may actually exist in the complex target nucleic acid. One reason for predicted lack of coverage in a region may be that a region expected to be in the complex target nucleic acid may actually not be present (e.g., a region may be deleted or re-arranged in the target nucleic acid), and thus not all oligonucleotides produced from the pool may isolate a fragment for inclusion in the second shotgun sequencing library.

Preferably, at least one oligonucleotide will be designed and created for each region identified for further analysis. More preferably, an average of three or more oligonucleotides will be provided for each region identified for further analysis.

It is a feature of the invention that the pool of oligonucleotides can be used directly to create the second shotgun sequencing library by polymerase extension of the oligonucleotides using templates derived from a target nucleic acid.

It is another feature of the invention that the pool of oligonucleotides can be used directly to create amplicons via circle dependent replication using the oligonucleotide pools and circle dependent replication.

It is another feature of the invention that the methods will provide sequencing information to identify absent regions of interest, e.g. predicted regions that were identified for analysis but which do not exist, e.g., due to a deletion or rearrangement.

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

BRIEF DESCRIPTIONS OF THE DRAWINGS

FIG. 9 is a schematic illustration of exemplary targeted nucleic acid segments, target-specific selection oligonucleotides and universal oligonucleotides in various stages of the claimed methods.

DEFINITIONS

Figure 1:
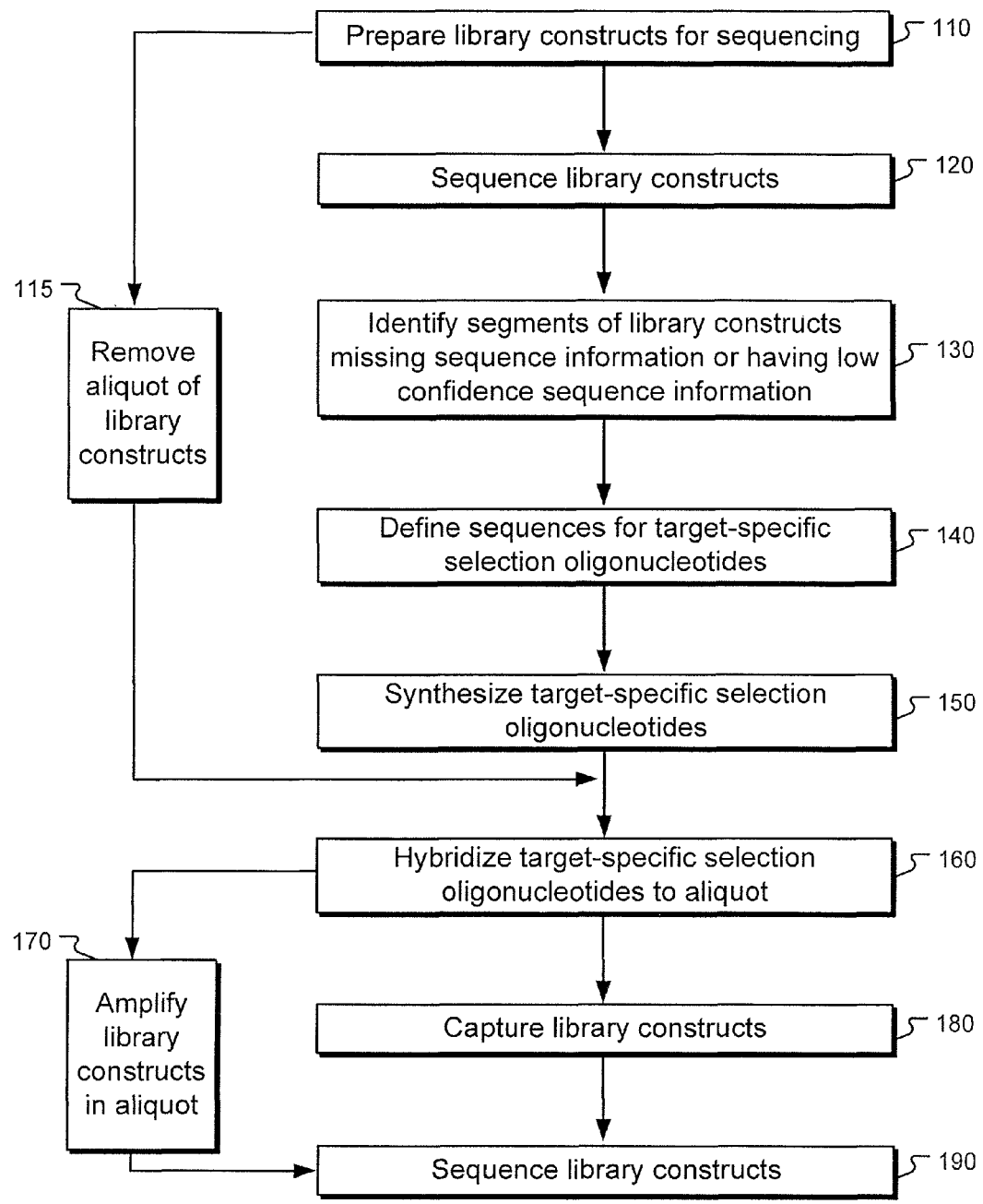
FIG. 1 is a simplified flow diagram of an exemplary method for sequencing nucleic acids using the processes of the claimed invention.

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Bowtell and Sambrook (2003), *DNA Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W.H. Freeman, New York N.Y.; Gait, "*Oligonucleotide Synthesis: A Practical Approach*" 1984, IRL Press, London; Nelson and Cox (2000), *Lehninger, Principles of Biochemistry* $3^{rd}$ Ed., W. H. Freeman Pub., New York, N.Y.; and Berg et al. (2002) *Biochemistry*, $5^{th}$ Ed., W.H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a target nucleic acid" refers to one or more copies of the target nucleic acid, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

In addition, many embodiments herein draw on disclosures described in. U.S. Ser. Nos. 11/451,691; 11/451,692; 11/679,124; 11/541,225; 60/776,415; 11/981,607; 11/938,096; 11/927,356; 11/938,106; 10/547,214; 11/934,695; 11/934,697; 11/934,703; 12/365,593; 12/266,385k 11/938,213 and 11/938,221; all of which are specifically incorporated by reference in their entirety.

"Adaptor" refers to an engineered construct comprising "adaptor elements" where one or more adaptors may be interspersed within target nucleic acid in a library construct. The adaptor elements or features included in any adaptor vary widely depending on the use of the adaptors, but typically include sites for restriction endonuclease recognition and/or cutting, sites for primer binding (for amplifying the library constructs) or anchor binding (for sequencing the target nucleic acids in the library constructs), nickase sites, and the like. In some aspects, adaptors are engineered so as to comprise one or more of the following: 1) a length of about 20 to about 250 nucleotides, or about 40 to about 100 oligonucleotides, or less than about 60 nucleotides, or less than about 50 nucleotides; 2) features so as to be ligated to the target nucleic acid as two "arms"; 3) different and distinct anchor binding sites at the 5' and the 3' ends of the adaptor for use in sequencing of adjacent target nucleic acid; and 4) one or more restriction sites.

"Amplicon" means the product of a polynucleotide amplification reaction. That is, it is a population of polynucleotides that are replicated from one or more starting sequences. Amplicons may be produced by a variety of amplification reactions, including but not limited to polymerase chain reactions (PCRs), linear polymerase reactions, nucleic acid sequence-based amplification, rolling circle amplification and like reactions (see, e.g., U.S. Pat. Nos. 4,683,195; 4,965,188; 4,683,202; 4,800,159; 5,210,015; 6,174,670; 5,399,491; 6,287,824 and 5,854,033; and US Pub. No. 2006/0024711, all of which are specifically incorporated by reference herein).

"Circle dependant replication" or "CDR" refers to multiple displacement amplification of a double-stranded circular template using one or more primers annealing to the same strand of the circular template to generate products representing only one strand of the template. In CDR, no additional primer binding sites are generated and the amount of product increases only linearly with time. The primer(s) used may be of a random sequence (e.g., one or more random hexamers) or may have a specific sequence to select for amplification of a desired product. Without further modification of the end product, CDR often results in the creation of a linear construct having multiple copies of a strand of the circular template in tandem, i.e. a linear, single-stranded concatamer of multiple copies of a strand of the template.

"Circle dependant amplification" or "CDA" refers to multiple displacement amplification of a double-stranded circular template using primers annealing to both strands of the circular template to generate products representing both strands of the template, resulting in a cascade of multiple-hybridization, primer-extension and strand-displacement events. This leads to an exponential increase in the number of primer binding sites, with a consequent exponential increase in the amount of product generated over time. The primers used may be of a random sequence (e.g., random hexamers) or may have a specific sequence to select for amplification of a desired product. CDA results in a set of concatemeric double-stranded fragments.

"Complementary" or "substantially complementary" refers to the hybridization or base pairing or the formation of a duplex between nucleotides or nucleic acids, such as, for instance, between the two strands of a double-stranded DNA molecule or between an oligonucleotide primer and a primer binding site on a single-stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the other strand, usually at least about 90% to about 95%, and even about 98% to about 100%.

"Duplex" means at least two oligonucleotides or polynucleotides that are fully or partially complementary and which undergo Watson-Crick type base pairing among all or most of their nucleotides so that a stable complex is formed. The terms "annealing" and "hybridization" are used interchangeably to mean formation of a stable duplex. "Perfectly matched" in reference to a duplex means that the poly- or oligonucleotide strands making up the duplex form a double-stranded structure with one another such that every nucleotide in each strand undergoes Watson-Crick base pairing with a nucleotide in the other strand. A "mismatch" in a duplex between two oligonucleotides or polynucleotides means that a pair of nucleotides in the duplex fails to undergo Watson-Crick base-pairing.

"Hybridization" refers to the process in which two single-stranded polynucleotides bind non-covalently to form a stable double-stranded polynucleotide. The resulting (usually) double-stranded polynucleotide is a "hybrid" or "duplex." "Hybridization conditions" will typically include salt concentrations of less than about 1M, more usually less than about 500 mM and may be less than about 200 mM. A "hybridization buffer" is a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are usually performed under stringent conditions, i.e., conditions under which a probe will hybridize to its target subsequence but will not hybridize to the other, uncomplimentary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. Exemplary stringent conditions include a salt concentration of at least 0.01 M to no more than 1M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of 30° C. are suitable for allele-specific probe hybridizations.

"Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide. Template driven ligation reactions are described in the following references: U.S. Pat. Nos. 4,883,750; 5,476,930; 5,593,826; and 5,871,921.

"Microarray" or "array" refers to a solid phase support having a surface, preferably but not exclusively a planar or substantially planar surface, which carries an array of sites containing nucleic acids such that each site of the array comprises identical copies of oligonucleotides or polynucleotides and is spatially defined and not overlapping with other member sites of the array; that is, the sites are spatially discrete. The array or microarray can also comprise a non-planar interrogatable structure with a surface such as a bead or a well. The oligonucleotides or polynucleotides of the array may be covalently bound to the solid support, or may be non-covalently bound. Conventional microarray technology is reviewed in, e.g., Schena, Ed. (2000), *Microarrays: A Practical Approach* (IRL Press, Oxford). As used herein, "random array" or "random microarray" refers to a microarray where the identity of the oligonucleotides or polynucleotides is not discernable, at least initially, from their location but may be determined by a particular operation on the array, such as by sequencing, hybridizing decoding probes or the like. See, e.g., U.S. Pat. Nos. 6,396,995; 6,544,732; 6,401,267; and 7,070,927; WO publications WO 2006/073504 and 2005/082098; and US Pub Nos. 2007/0207482 and 2007/0087362.

"Nucleic acid", "oligonucleotide", "polynucleotide", "oligo" or grammatical equivalents used herein refer generally to at least two nucleotides covalently linked together. A nucleic acid generally will contain phosphodiester bonds, although in some cases nucleic acid analogs may be included that have alternative backbones such as phosphoramidite, phosphorodithioate, or methylphosphoroamidite linkages; or peptide nucleic acid backbones and linkages. Other analog nucleic acids include those with bicyclic structures including locked nucleic acids, positive backbones, non-ionic backbones and non-ribose backbones. Modifications of the ribose-phosphate backbone may be done to increase the stability of the molecules; for example, PNA:DNA hybrids can exhibit higher stability in some environments. As used herein, "targeted nucleic acid segment" refers to a nucleic acid targeted for re-sequencing in Phase II of the methods. "Target-specific selection oligonucleotide" refers to the oligonucleotide probe used in Phase II of the sequencing methods that has a sequence complementary to a targeted nucleic acid segment. "Universal oligonucleotide" refers to an oligonucleotide probe used in some aspects of Phase II of the methods, having a "universal" sequence (e.g., a set of degenerative nucleotides, and/or one or more universal bases), one or more specific bases, and, in some aspects, a 5' functional group such as biotin, and a 3' phosphate.

"Primer" means an oligonucleotide, either natural or synthetic, which is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a DNA polymerase.

"Probe" means generally an oligonucleotide that is complementary to an oligonucleotide or target nucleic acid under investigation. Probes used in certain aspects of the claimed invention are labeled in a way that permits detection, e.g., with a fluorescent or other optically-discernable tag.

"Sequence determination" in reference to a target nucleic acid or a targeted nucleic acid segment means determination of information relating to the sequence of nucleotides in the target nucleic acid. Such information may include the identification or determination of partial as well as full sequence information of the target nucleic acid. The sequence information may be determined with varying degrees of statistical reliability or confidence. In one aspect, the term includes the determination of the identity and ordering of a plurality of contiguous nucleotides in a target nucleic acid starting from different nucleotides in the target nucleic acid.

"Shotgun library" means a mixture of more than 1,000, or more than 3,000 or more than 10,000 or more than 30,000 distinct target nucleic acid fragments, each represented on average multiple times. A shotgun library may represent a, e.g., genome, metagenome or transcriptome; alternatively, a shotgun library may represent selected regions of a genome, metagenome or transcriptome.

"Target nucleic acid" means a nucleic acid from a gene, a regulatory element, genomic DNA, cDNA, RNAs including mRNAs, rRNAs, siRNAs, miRNAs and the like and fragments thereof. A target nucleic acid may be a target nucleic acid from a sample, or a secondary target such as a product of an amplification reaction.

As used herein, the term "$T_m$" is commonly defined as the temperature at which half of the population of double-stranded nucleic acid molecules becomes dissociated into single strands. The equation for calculating the $T_m$ of nucleic acids is well known in the art. As indicated by standard references, a simple estimate of the $T_m$ value may be calculated by the equation: $T_m = 81.5 + 16.6(\log 10[Na^+])0.41(\%[G+C]) - 675/n - 1.0$ m, when a nucleic acid is in aqueous solution having cation concentrations of 0.5 M, or less, the (G+C) content is between 30% and 70%, n is the number of bases, and m is the percentage of base pair mismatches (see e.g., Sambrook J et al. (2001), *Molecular Cloning, A Laboratory Manual*, 3rd Ed., (Cold Spring Harbor Laboratory Press)). Other references include more sophisticated computations, which take structural as well as sequence characteristics into account for the calculation of $T_m$ (see also, Anderson and Young (1985), "Quantitative Filter Hybridization", *Nucleic Acid Hybridization*, and Allawi and SantaLucia (1997), Biochemistry 36:10581-94).

DETAILED DESCRIPTION

Technology is described herein for providing efficient sequencing of complex samples of target nucleic acids. This technology is sometimes referred to herein as "shotgun sequencing". Typically, shotgun sequencing of a sample nucleic acid requires a high redundancy of reads (e.g. "base calls") to be able to determine every base in the sample with sufficient confidence. Most of the effort in traditional shotgun sequencing processes goes into sequencing the last few percent of bases, especially when there is a sequence bias in the library of constructs. Even with the most efficient sequencing methods, there is a cost-driven need to reduce the redundancy from about 100× genome coverage to about 10-20× genome coverage, yet this must be accomplished without missing any sequence. Complete sequencing (i.e., 100% coverage) is particularly important in diagnostics because if a region of a nucleic acid sample is missed, the results are deemed incomplete and may not be relied upon; thus the methods claimed herein are applicable to diagnostic procedures. Similarly, complete and accurate sequencing can be quite important in single nucleotide polymorphism (SNP) detection and correlation to disease states.

Methods provided herein solve the redundancy problem of shotgun sequencing by employing a "two-phase" or "multi-phase" sequencing approach. In Phase I, an appropriate read coverage such as, e.g., 5-15×, is processed and assembled, using any number of techniques, including, but not limited to, those techniques outlined in U.S. Ser. Nos. 11/451,691; 11/451,692; 11/679,124; 11/541,225; 60/776,415; 11/981,607; 11/938,096; 11/927,356; 11/938,106; 10/547,214; 11/934,695; 11/934,697; 11/934,703; 12/365,593; 12/266,385k 11/938,213 and 11/938,221; all of which are specifically incorporated by reference in their entirety and in particular for sequencing methods such as sequencing by ligation.

Based on sequence assembly information from the initial read, missing sequence from regions of the target nucleic acid or low confidence sequence reads from regions of the target nucleic acid, for example, are identified and targeted for further study. These sequences are sometimes referred to herein as "sequences of interest" or "incomplete sequences". As will be appreciated by those in the art, there may be one sequence of interest or multiple sequences of interest. In general, the sequences of interest are a set of sequences separated in the original genome or target sequence. Sets of sequences of interest may be about 100 different incomplete sequences, about 500, about 1000, about 5,000, about 10,000, about 20,000, about 50,0000, about 75,000 or about 100,000 different incomplete sequences.

The logic for this approach is that in Phase II, about 1-10% of the initial target nucleic acid that is missing sequence or that otherwise needs sequence confirmation is selected and sequenced at approximately 100× coverage. The effort to sequence 1-10% at 100× in Phase II is equivalent to sequencing 1-10× of the entire genome. The two sequencing phases combined thus result in about a 10-25× redundancy, reducing the overall effort 4-10× relative to 100× coverage of the entire genome. For the two-phase approach to be practical, the selection reagents, selection process and additional nucleic acid processing of Phase II preferably should cost less than sequencing about 10× of the genome, and more preferably less than about 5×.

In addition, in many circumstances only a small percentage of sequence of a sample (e.g., a small percentage of a genome, transcriptome or meta-genome) is of interest. In such circumstances, sequencing a library that is enriched in target sequences of interest rather than sequencing an entire sample is desirable. Due to the low cost and high throughput of random DNA array-based sequencing methods, the selection of sequences of interest need not be very efficient to be both result and cost effective. For example, if there is a need to sequence only 1% of the genome, sequencing the 10% of the genome that contains the targeted 1% still provides a 10× improvement relative to sequencing the entire genome. Thus, targeting the sequences of interest via pre-sequencing enrichment is desirable.

Furthermore, even given small error rates in the sequence data, low mutation rates can lead to a majority of the detected variants being false calls in the sequence(s) of interest. For example, at a given error rate of 1 per Mb, and a given "preserved" mutation rate in various functional parts of the cancer genome, this can lead to the following false calls:

|  | Non-coding | All coding changes | Non-synonymous changes |
| --- | --- | --- | --- |
| Errors/Mb | 1 | 1 | ~0.3 |
| Mutations/Mb | 2 | 1 | ~0.1* |
| % wrong | 33% | 50% | 75% |
| Errors/Mb | 0.1 | 0.1 | ~0.03 |
| Mutations/Mb | 2 | 1 | ~0.1* |
| % wrong | 4.5% | 9% | 25% |

*Actual data was 10 mutations in 60 Gb of exons where there should have been 6

FIG. 1 is a simplified flow diagram of one aspect of an overall method 100 for sequencing nucleic acids of interest using the processes of the claimed invention. The described process relies on the use of arrays of DNA nanoballs ("DNBs") and sequencing by hybridization as the platform for sequencing, but it should be appreciated that the description is not so limited and can utilize other sequencing platforms. The various processes will be described briefly first, with each process described in more detail infra, using the reference numbers of FIG. 1.

The general process used to create the DNB arrays is as described in U.S. Ser. No. 11/679,124, hereby incorporated by reference in its entirety. As an overview, the general methods and compositions of the DNB arrays are used for acquiring nucleotide sequence information of target sequences (also referred to herein as "target polynucleotides") using adaptors interspersed in target polynucleotides. The sequence information can be new, e.g. sequencing unknown nucleic acids, resequencing, or genotyping. In general, a plurality of adaptors are inserted at spaced locations within a target polynucleotide or a fragment of a polynucleotide. Such adaptors are referred to herein as "interspersed adaptors", and may serve as platforms for interrogating adjacent sequences using various sequencing chemistries, such as those that identify nucleotides by primer extension, probe ligation, and the like. That is, one unique component of some embodiments of the invention is the insertion of known adaptor sequences into target sequences, such that there is an interruption of contiguous target sequence with the adaptors. By sequencing both "upstream" and "downstream" of the adaptor, sequence information of entire target sequences may be accomplished (e.g. the "first shotgun library"). In general, the arrays are made as follows (it should be noted that genomic DNA is used as an example herein, but is not meant to be limiting). Genomic DNA from any organism is isolated and fragmented into target sequences using standard techniques. A first adaptor is ligated to one terminus of the target sequence. The adaptor preferably comprises a Type IIs restriction endonuclease site, which cuts outside of the recognition sequence. If the enzyme results in a "sticky" end, the overhang portion can either be filled in or removed.

In one embodiment, an enzyme is used to ligate the two ends of the linear strand comprising the adaptor and the target sequence to form a circularized nucleic acid. This may be done using a single step. Alternatively, a second adaptor can be added to the other terminus of the target sequence (for example, a polyA tail), and then a bridging sequence can be hybridized to the two adaptors, followed by ligation. In either embodiment, a circular sequence is formed.

The circular sequence is then cut with the Type IIs endonuclease, resulting in a linear strand, and the process is repeated. This results in a circular sequence with adaptors interspersed at well defined locations within previously contiguous target sequences.

The circularized sequences are then amplified using a rolling circle replication (RCR) reaction, to form concatemers of the original target sequence (e.g. multimers of monomers). These long concatemers form "DNA nanoballs" ("DNBs") can then optionally be immobilized on a surface in a variety of ways, as outlined below and in U.S. Ser. No. 11/679,124 and other applications referenced herein.

Once on the surface, using the known adaptor sequences, sequencing of the intervening target sequences is done. As is known in the art, there are a number of techniques that can be used to detect or determine the identity of a base at a particular location in a target nucleic acid, including, but not limited to, the use of temperature, competitive hybridization of perfect and imperfect probes to the target sequence, sequencing by synthesis, for example using single base extension techniques (sometimes referred to as "minisequencing"), the oligonucleotide ligase amplification (OLA) reaction, rolling circle replication (RCR), allelic PCR, competitive hybridization and Invader™ technologies. Preferred embodiments include sequencing by hybridization with ligation, and sequencing by hybridization.

The sequence information can then be used to reconstruct sequences of larger target sequences, such as sequencing of the entire genomic DNA.

With reference to FIG. 1, nucleic acids are prepared for sequencing by extracting and fractionating (e.g., shearing or cleaving) target nucleic acids as noted herein. A library is then constructed (110) with the fractionated target nucleic acids using engineered adaptors, where the library constructs are assembled by inserting adaptors at a multiplicity of sites throughout each target nucleic acid fragment. The interspersed adaptors permit acquisition of sequence information from multiple sites in the target nucleic acid consecutively or simultaneously. In some aspects of the methods, an aliquot of the library constructs is saved for Phase II sequencing (115). Next, the library constructs are sequenced in an initial Phase I sequencing procedure (120). The sequence assembly information from the Phase I sequencing process is then used to identify segments of the target nucleic that have missing sequence information or the sequence information is questionable (i.e., low confidence information) (130). Once targeted nucleic acid segments are identified, sequences for the target-specific selection oligonucleotides to be used in Phase II of the sequencing process are defined (140) and these target-specific selection oligonucleotides are synthesized (150).

In process 160, target-specific selection oligonucleotides are combined with and hybridized to the library constructs containing the targeted nucleic acid segments in the aliquot. Next, in an alternative embodiment, universal oligonucleotides are hybridized to the target-specific selection oligonucleotide:library construct hybrids, and ligated to the target-specific selection oligonucleotides in process 170. The library constructs containing targeted nucleic acid segments that have hybridized to the ligated target-specific selection oligonucleotides (and universal oligonucleotides, in the alternative embodiment) are then captured (180) and sequenced (190). Optionally, in this aspect, the captured library constructs from process 180 are amplified, e.g., by circle dependent amplification (not shown) before being sequenced (190).

In an alternative aspect of the methods, after the target-specific selection oligonucleotides are hybridized to the library constructs containing the targeted nucleic acid segments in the aliquot (160), the target-specific oligonucleotides are used as primers for circle dependent replication (175) to form nucleic acid amplicons (coiled linear repeats of adaptor and target nucleic acids), that are then sequenced in process 190.

Figure 2:
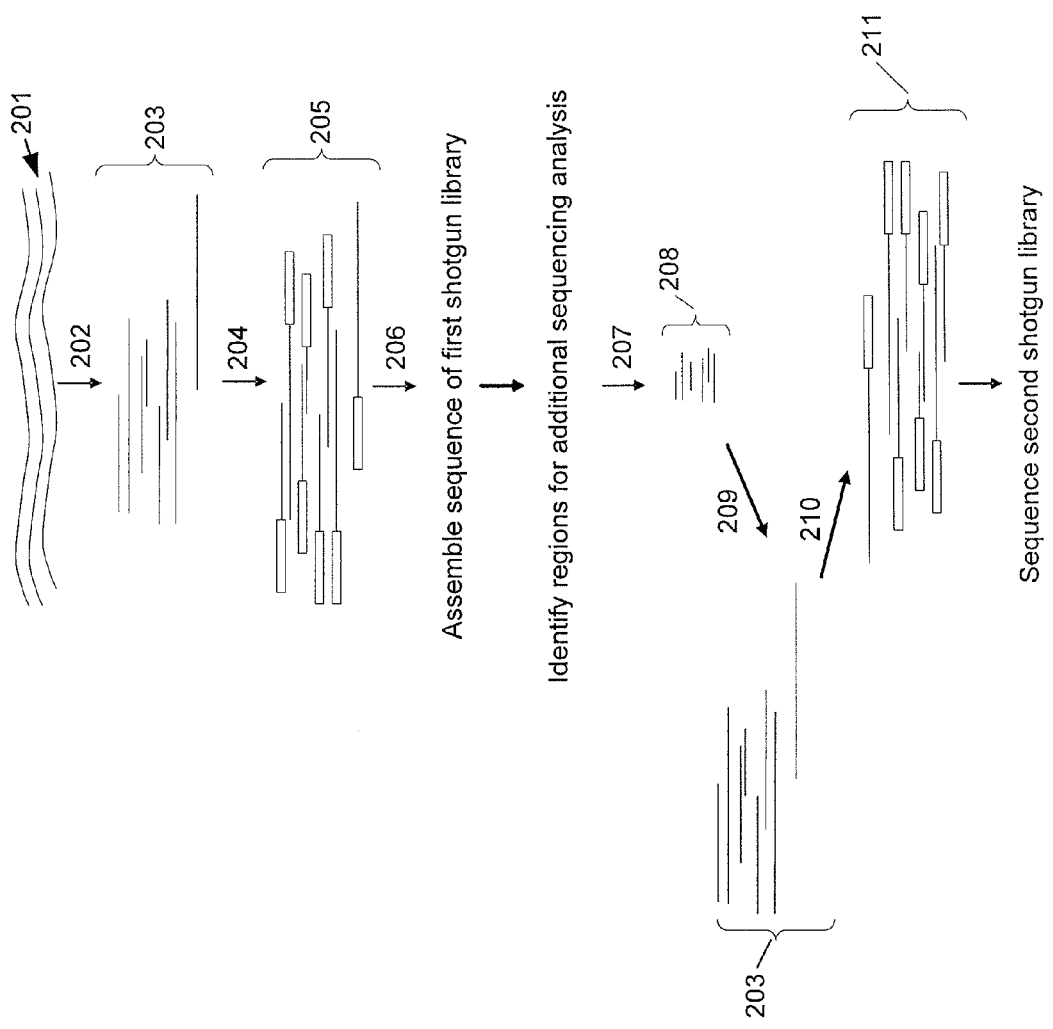
FIG. 2 is a general schematic representation of a method for sequencing nucleic acids using the processes of the claimed invention.

FIG. 2 is a general schematic representation of a method for sequencing nucleic acids using the processes of the claimed invention. In FIG. 2, complex target nucleic acid 201 is prepared for sequencing 202, by, for example, shearing, sonication or fractionation to produce redundant fragments of the target nucleic acid 203. The fragments of complex target nucleic acid are then ligated to adaptors 204 to form a first shotgun library 205. The processes for library formation are discussed in detail infra. Next, the first shotgun library is sequenced (at, for example a 5-40× coverage) 206, and the sequence reads are assembled. The assembled sequence is then analyzed, and regions of the complex target nucleic acid are identified for additional sequencing analysis (e.g., for SNP analysis, to provide additional coverage for certain regions or to resolve conflicting sequence reads from certain regions (low confidence regions), and/or to provide missing sequence information). Target-specific selection oligonucleotides are then synthesized based on the regions of complex target nucleic acid identified 207 as being of interest for further analysis. The target-specific oligonucleotides are then combined with complex target nucleic acids (e.g., a portion of the original sample as shown here, or alternatively, an aliquot of the first shotgun library from some stage of preparation of the first shotgun library), and used to select and amplify the regions of interest in the complex target nucleic acids 209, resulting in amplified regions of the complex target nucleic acid. The amplified regions of complex target nucleic acid are then ligated to adaptors 210 to form a second shotgun library 211, which is then sequenced 212, and the sequence reads are assembled.

Figure 3:
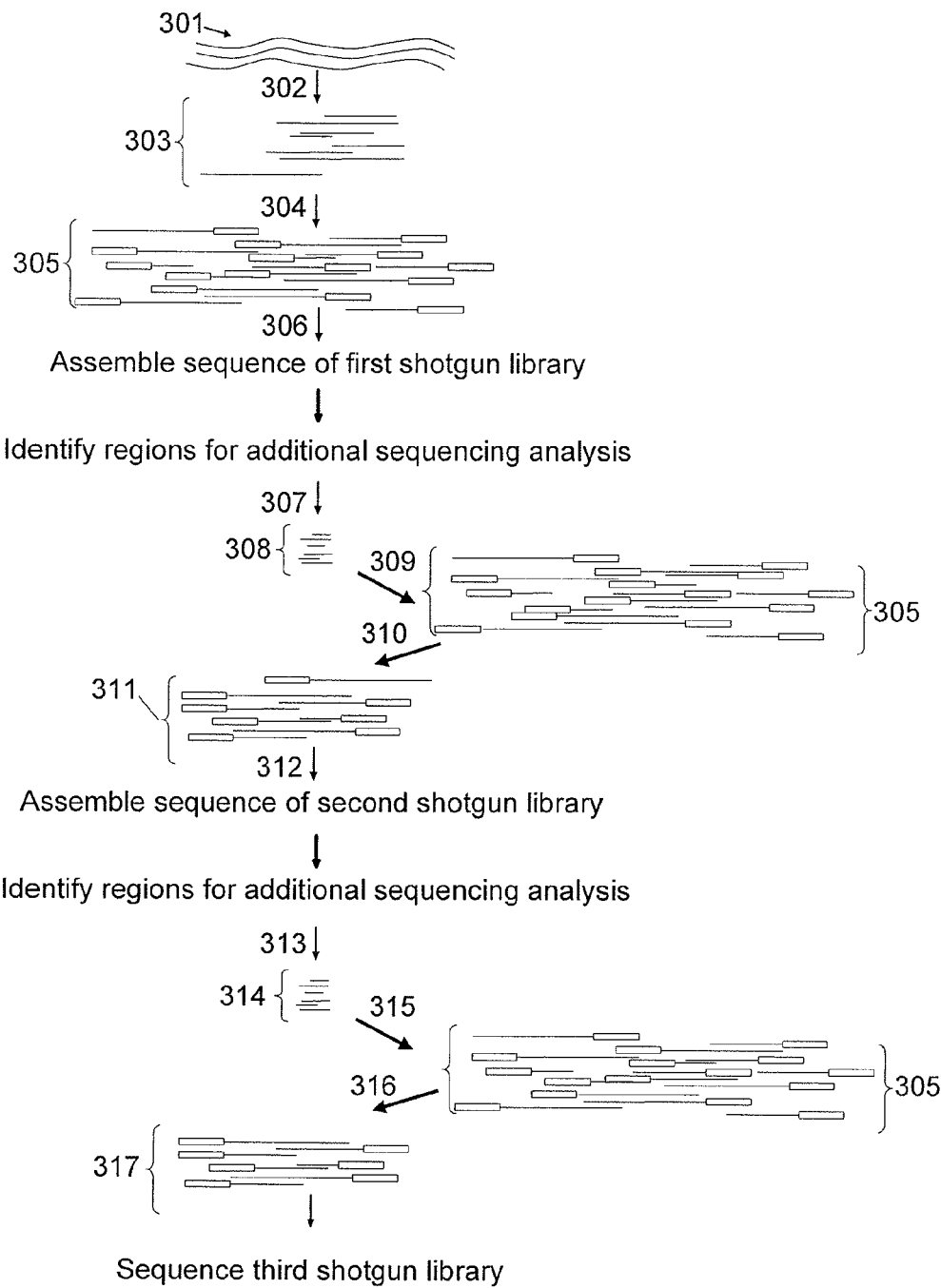
FIG. 3 is a general schematic representation of yet another method for sequencing nucleic acids using the processes of the claimed invention.

FIG. 3 is a general schematic representation of another method for sequencing nucleic acids using the processes of the claimed invention. In FIG. 3, complex target nucleic acid 301 is prepared for sequencing 302 to produce redundant fragments of the complex target nucleic acid 303. The fragments of complex target nucleic acid are then ligated to adaptors 304 to form a first shotgun library 305. The first shotgun library is then sequenced (at, for example a 5-40× coverage) 306, and the sequence reads are assembled. As described for FIG. 2, the assembled sequence is then analyzed, and regions of interest of the complex target nucleic acid are identified for additional sequencing analysis. Target-specific selection oligonucleotides are then synthesized 307 based on the regions of complex target nucleic acid identified as being of interest for further analysis. The target-specific selection oligonucleotides 307 are then combined with complex target nucleic acids (e.g., here, an aliquot of the first shotgun library 305), and used to select and amplify the regions of interest in the complex target nucleic acids from the first shotgun library 305, resulting in amplified regions of the complex target nucleic acid. The amplified regions of complex target nucleic acid are then ligated to adaptors 310 to form a second shotgun library 311, which is then sequenced 312, and the sequence reads are assembled. Again, sequence information—this time from the second shotgun library—is used to identify regions of interest in the complex target nucleic acid for further analysis, and a new set of target-specific selection oligonucleotides 314 are synthesized 313. The target-specific selection oligonucleotides 314 are then combined with complex target nucleic acids (e.g., here again, an aliquot of the first shotgun library 305, but other alternatives include using original sample, or using the second shotgun library may be employed), and used to select and amplify the second round regions of interest in the complex target nucleic acids from the first shotgun library 305, resulting in amplified regions of the complex target nucleic acid. The amplified regions of target nucleic acid are then ligated to adaptors 310 to form a third shotgun library 311, which is then sequenced 312, and the sequence reads are assembled. The processes here may be repeated any number of times to acquire sequence tot a confidence level of choice.

Preparation of Library Constructs (FIG. 1, Process 110)

Figure 4:
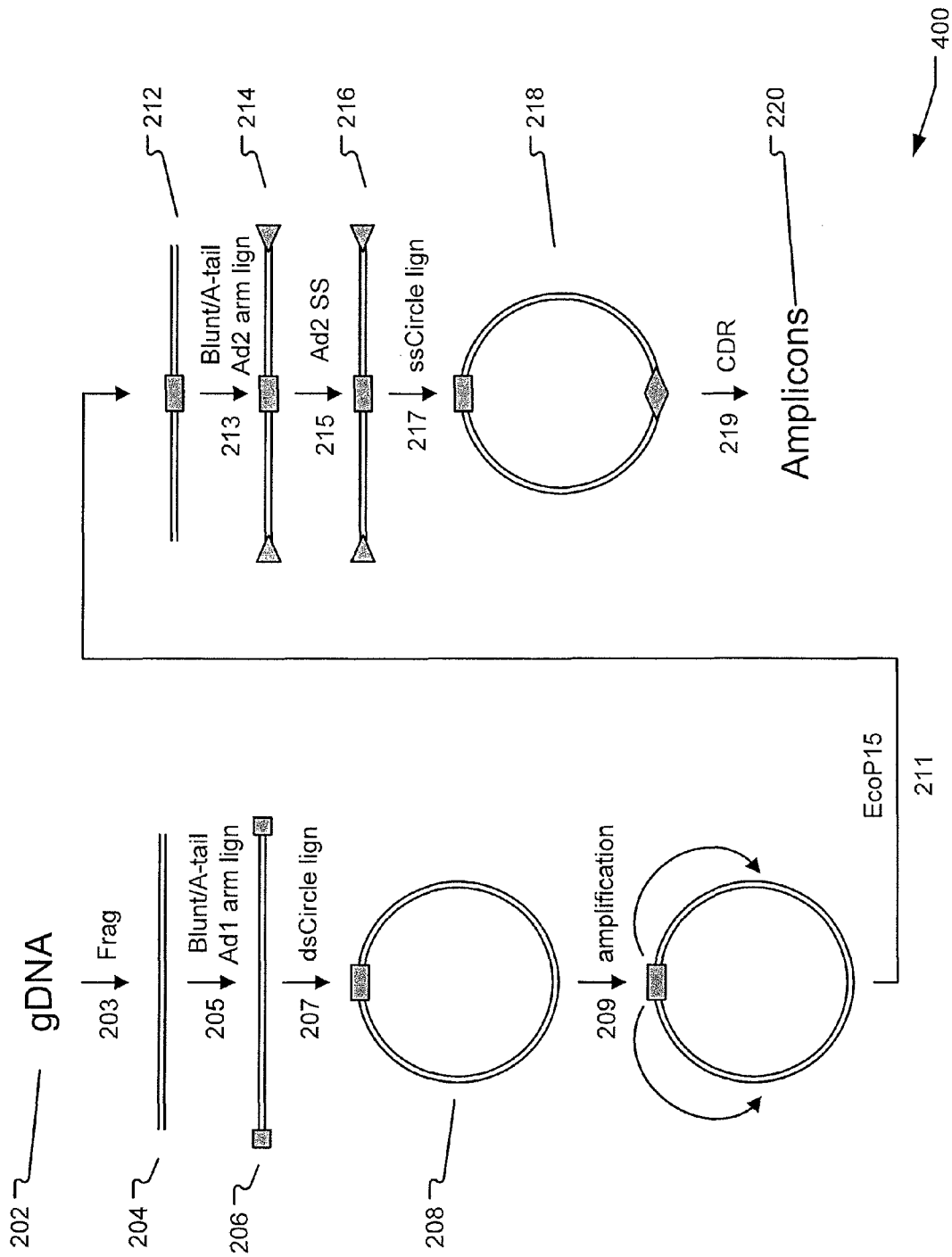
FIG. 4 is a schematic representation of one aspect of a method for assembling adaptor/target nucleic acid library constructs.

FIG. 4 is a schematic representation of one aspect of a method for assembling adaptor/target nucleic acid library constructs. DNA, such as genomic DNA 402, is isolated and prepared 403 to produce target nucleic acids 404 using standard techniques. The target genomic DNA is isolated using conventional techniques, for example as disclosed in Sambrook and Russell, *Molecular Cloning: A Laboratory Manual*, cited supra. The target genomic DNA is then fractionated or fragmented to a desired size by conventional techniques including enzymatic digestion, shearing, or sonication. Fragment size of the target nucleic acid can vary depending on the source target nucleic acid and the library construction methods used, but typically ranges from 50 nucleotides in length to over 11 kb in length, including 200-700 nucleotides in length, 400-600 nucleotides in length, 450-550 in length, or 4 kb to over 10 kb in length. Alternatively, in some aspects, the target nucleic acids comprise mRNAs or cDNAs. In specific embodiments, the target nucleic acids are created using isolated transcripts from a biological sample. Isolated mRNA may be reverse transcribed into cDNAs using conventional techniques, again as described in *Genome Analysis: A Laboratory Manual Series* (Vols. I-IV) or *Molecular Cloning: A Laboratory Manual*.

In some aspects of the methods, the fragmented target nucleic acids 404 are then repaired so that the 5' and 3' ends of each strand are flush or blunt ended. Following this reaction, each fragment is "A-tailed" with a single A added to the 3' end of each strand of the fragmented target nucleic acids using a non-proofreading polymerase 405. Also as part of process 405, a first and second arm of a first adaptor is then ligated to each target nucleic acid, producing a target nucleic acid with adaptor arms ligated to each end 406. In one aspect, the adaptor arms are "T tailed" to be complementary to the A tailing of the target nucleic acid, facilitating ligation of the adaptor arms in a known orientation. Similarly, G/C tailing can be performed.

In a preferred embodiment, the invention provides adaptor ligation to each fragment in a manner that minimizes the creation of intra- or intermolecular ligation artifacts. This is desirable because random fragments of target nucleic acids forming ligation artifacts with one another create false proximal genomic relationships between target nucleic acid fragments, complicating the sequence alignment process. The aspect shown in FIG. 4 shows step 405 as a combination of blunt end repair and an A tail addition. This preferred aspect using both A tailing and T tailing to attach the adaptor to the DNA fragments prevents random intra- or inter-molecular associations of adaptors and fragments, which reduces artifacts that would be created from self-ligation, adaptor-adaptor or fragment-fragment ligation.

As an alternative to MT tailing (or G/C tailing), various other methods can be implemented to prevent formation of ligation artefacts of the target nucleic acids and the adaptors, as well as position and orient the adaptor arms with respect to the target nucleic acids, including using complementary NN overhangs in the target nucleic acids and the adaptor arms, or employing blunt end ligation with an appropriate target nucleic acid to adaptor ratio to optimize single fragment nucleic acid/adaptor arm ligation ratios or using the nick translation-type process as described infra.

In process 407, the linear target nucleic acid 406 is circularized, resulting in a circular library construct 408 comprising target nucleic acid and an adaptor. Note that the circularization process results in bringing the first and second arms of the first adaptor together to form a contiguous adaptor sequence in the circular construct. In process 409, the circular construct is amplified, such as by circle dependent amplification, using, e.g., random hexamers and φ29 or helicase. Alternatively, target nucleic acid/adaptor structure 406 may remain linear, and amplification may be accomplished by PCR primed from sites in the adaptor arms. The amplification 409 preferably is a controlled amplification process and uses a high fidelity, proof-reading polymerase, resulting in a sequence-accurate library of amplified target nucleic acid/adaptor constructs where there is sufficient representation of the genome or one or more portions of the genome being queried.

In aspects herein, the first adaptor comprises two Type IIs restriction endonuclease recognition sites, positioned such that the target nucleic acid outside the recognition sequence (and outside of the adaptor) is cut 410. The arrows around structure 410 indicate the recognition sites and the site of restriction. In process 411, EcoP15, a Type IIs restriction endonuclease, is used to cut the library constructs. Note that in the aspect shown in FIG. 4, a portion of each library construct mapping to a portion of the target nucleic acid will be cut away from the construct (the portion of the target nucleic acid between the arrow heads in structure 410). Restriction of the library constructs with EcoP15 in process 411 results in a library of linear constructs containing the first adaptor, with the first adaptor "interior" to the ends of the linear construct 412. The resulting linear library construct will have a size defined by the distance between the endonuclease recognition sites and the endonuclease restriction site plus the size of the adaptor. In process 413, the linear construct 412, like the fragmented target nucleic acid 404, is treated by conventional methods to become blunt or flush ended, A tails comprising a single A are added to the 3' ends of the linear library construct using a non-proofreading polymerase and first and second arms of a second adaptor are ligated to ends of the linearized library construct by A-T tailing and ligation 413. Similarly G-C tailing can be performed. The resulting library construct comprises the structure seen at 414, with the first adaptor interior to the ends of the linear construct, with target nucleic acid flanked on one end by the first adaptor, and on the other end by either the first or second arm of the second adaptor.

In process 415, the double-stranded linear library constructs are treated so as to become single-stranded 416, and the single-stranded library constructs 416 are then ligated 417 to form single-stranded circles of target nucleic acid interspersed with two adaptors 418. The ligation/circularization process of 417 is performed under conditions that optimize intramolecular ligation.

Next, in the two-adaptor aspect shown in FIG. 4, the single-stranded, circularized library constructs 418 are amplified by circle dependent replication 419 to form DNA amplicons ("amplicons") 420. Circle dependent replication is performed, e.g., using specific primers where the amplification product displaces its own tail, producing linear, tandem single-stranded copies of l-target nucleic acid/adaptor 1/target nucleic acid/adaptor 2-l library concatemers. Single-stranded DNA concatemers under conventional conditions (in buffers, e.g., TE, SSC, SSPE or the like) form random coils in a manner known in the art (e.g., see Edvinssom (2002), "On the size and shape of polymers and polymer complexes," Dissertation 696 (University of Uppsala)). Thus, as the tandem copies begin to multiply, the library constructs begin to coil and form secondary structures, ultimately forming the DNA amplicons. Each library construct contains in some aspects between about ten to about 5000 copies, or from about 250 copies to about 2500 copies of the l-target nucleic acid/adaptor 1/target nucleic acid/adaptor 2-l repeats, and preferably contains about 500 to about 1200 copies of the l-target nucleic acid/adaptor 1/target nucleic acid/adaptor 2-l repeats. The resulting DNA amplicons 420, then, are clonal populations of DNA in discrete structures, which can then be arrayed and sequenced (process not shown).

In some aspects of the methods described herein, the adaptors are oriented with respect to one another in a pre-selected fashion, as the inability to control the orientation of adaptors with respect to one another can have a number of undesired consequences. The presence of adaptors in both orientations in a population of target nucleic acid/adaptor library constructs may require multiple sequencing primers in each sequencing reaction to enable sequencing regardless of the orientation of a given adaptor. In addition, analysis of sequence data collected from multiple adaptors of unspecified orientation may require either determination of the orientation of each adaptor or consideration of all possible combinations of adaptor orientation during assembly. Thus, in addition to directing the relative position of inserted adaptors to one another, it is desirable in some aspects to direct the relative orientation of subsequently-inserted adaptors as well.

Figure 5:
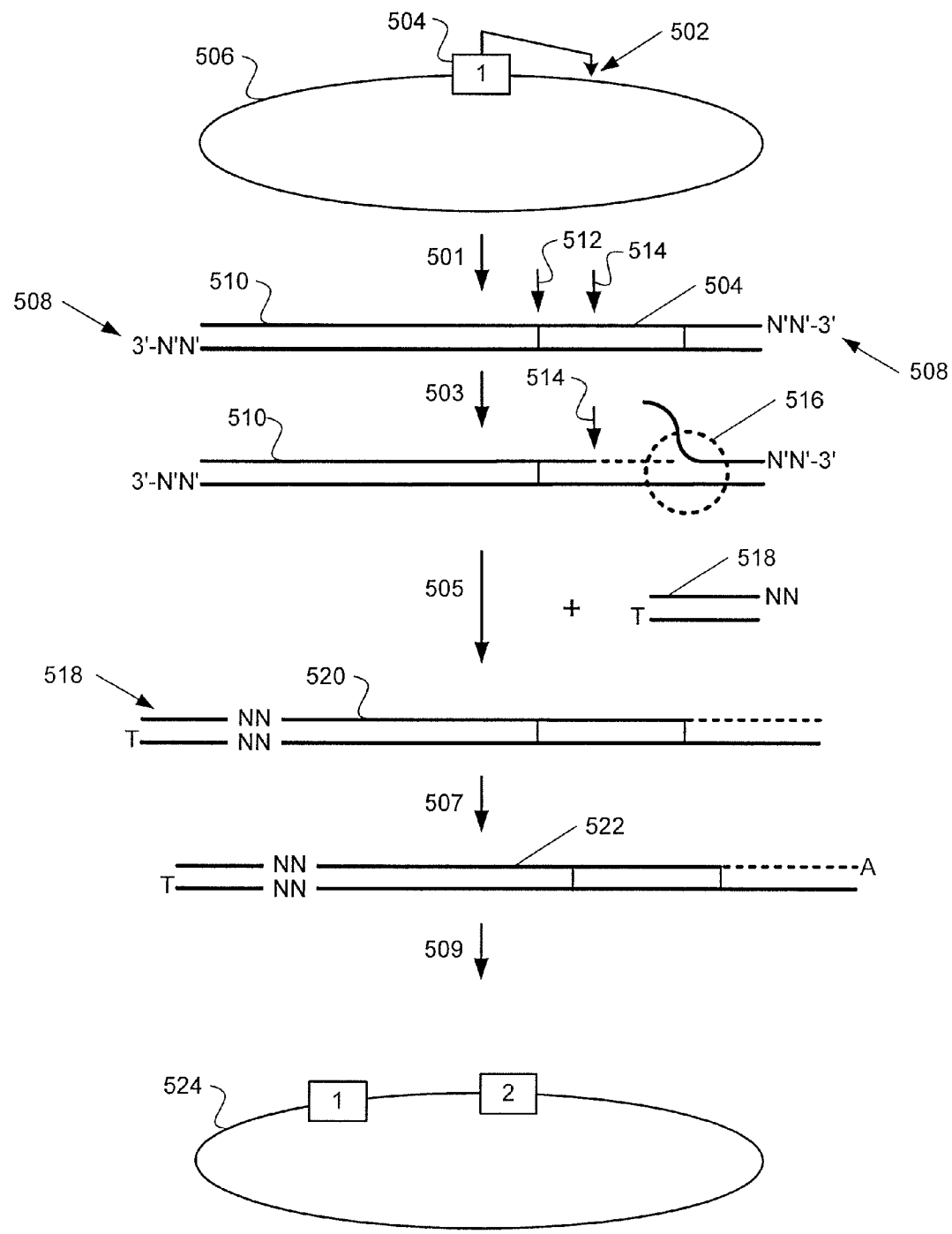
FIG. 5 is a schematic representation of a process where a nick translation-type process is used to control the orientation with which a second adaptor is inserted with respect to a first adaptor.

FIG. 5 shows one method for inserting adaptors in an orientation-specific manner with respect to one another that can be used in conjunction with the methods for making library constructs described herein and illustrated schematically in FIG. 4. For example, after restriction digest 411 of FIG. 4 and before adaptor ligation 413, the "nick translation" type process shown in FIG. 5 can be performed. In the case of the process shown in FIG. 4, a library construct has been formed that is circular and has one interspersed adaptor, similar to 504 in FIG. 5, with a restriction endonuclease recognition site at the tail of the arrow in FIG. 5, and a site of restriction at 502.

The library constructs with an inserted first adaptor are digested by a restriction endonuclease process 501—in preferred aspects, a Type IIs restriction endonuclease—that cuts the target nucleic acid to render 3' nucleotide overhangs 508. In FIG. 5, two nucleotides (NN-3') 508 are shown, though the number of overhanging nucleotides varies in alternative aspects. The library construct 510 is linearized, with the first inserted adaptor shown at 504. The first inserted adaptor 504 is engineered such that it comprises either a nick 512 at the boundary of the adaptor fragment or it comprises the recognition site for a nicking endonuclease that permits the introduction of a nick 514 at the interior of the adaptor. In either case, library construct 510 is treated 503 with a polymerase 516 that can extend the upper strand from nick 512 or 514 to the end of the lower strand of library construct 510 to form a strand having a 3' overhang at one end and a blunt end at the other. To this library construct 510, a second adaptor 518 is ligated in process 505, where the second adaptor 518 has a degenerate nucleotide overhang at one end and a single 3' nucleotide (e.g., dT) overhang at the other end to form library construct 520. Library construct 520 is then treated (e.g., with Taq polymerase) in process 507 to add a 3' dA to the blunt end.

Library construct 522 may then be amplified by PCR, with, e.g., uracil-containing primers. Alternatively, library construct 522 may then be circularized in process 509 in which case RCA may be performed.

In some aspects, a portion or aliquot of the library constructs are saved for Phase II selection and sequencing (as shown in process 115 of FIG. 1). The aliquot may be taken at an early, intermediate, or late step in the library construct preparation process depending on the purpose of the Phase II sequencing effort and the desire to retain an unbiased, more uniform sequence representation of the sample. There are two characteristics to be considered when choosing the nucleic acids for some aspects of Phase II re-sequencing (i.e., choosing the targeted nucleic acid segments). First, the aliquot preferably should comprise redundant overlapped DNA fragments for each desired targeted nucleic acid segment. Second, the library constructs saved for sequencing in Phase II preferably comprise a stretch of nucleic acid long enough to allow for the flexible design of efficient and specific target-specific selection oligonucleotides. One example is to prepare library constructs with an initial and two consecutively-inserted adaptors allowing reads of 12+12 bases at, e.g., the 5' end of the library constructs with up to 200-1000 bases, or as high as about 10,000 bases at the, e.g., 3' end of the library constructs.

Figure 6:
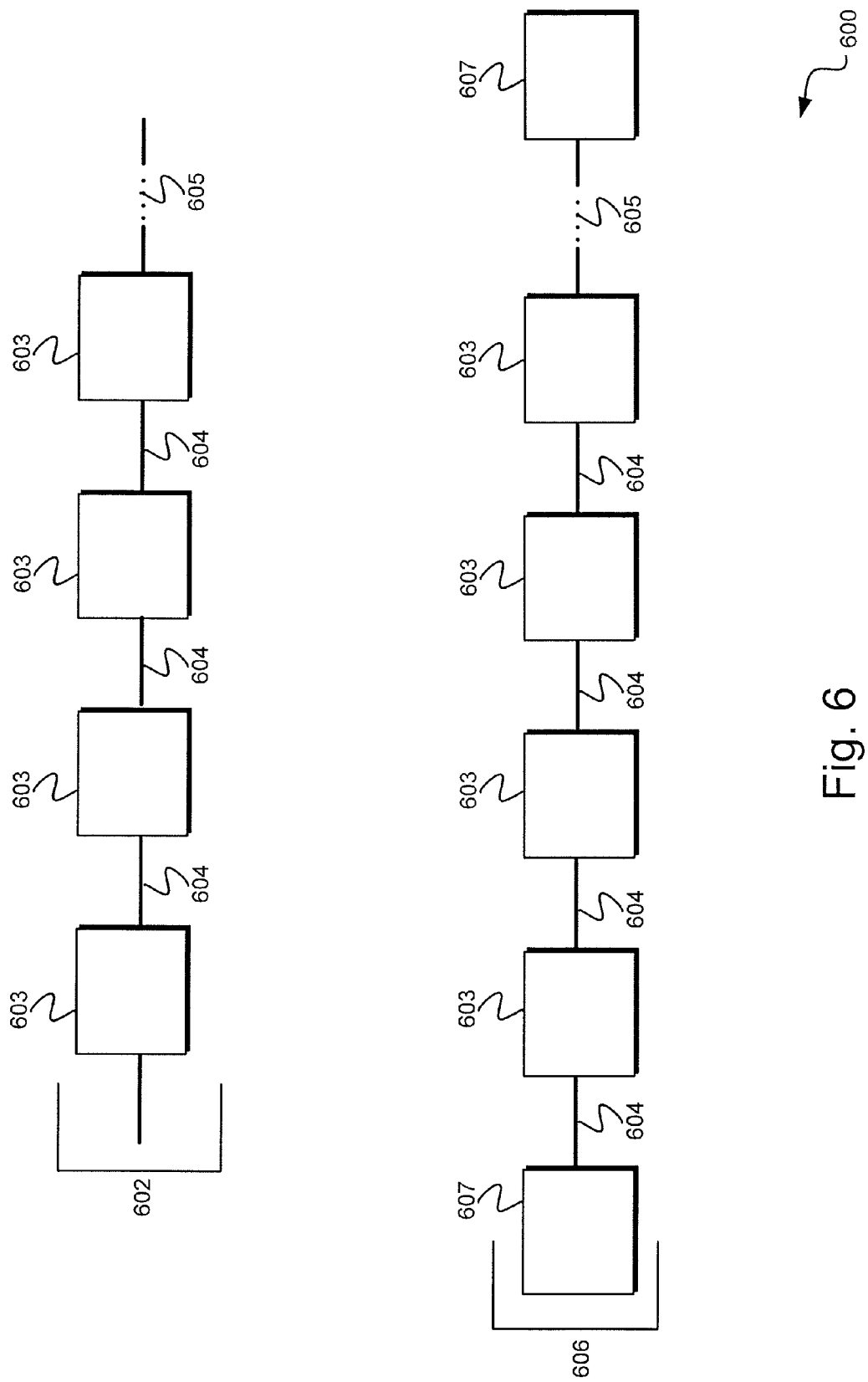
FIG. 6 is a schematic representation of library constructs to be used for target-specific selection oligonucleotide design and Phase II selection and sequencing according to the claimed methods.

FIG. 6 is a schematic representation of library constructs to be used in a target-specific selection oligonucleotide design, and Phase II selection and sequencing according to the claimed methods. FIG. 6 shows a linearized library construct 602, comprising interspersed adaptors 603 ranging in length from about 20 to about 30 bases, targeted nucleic acid segments 604 ranging in length from about 12 to about 24 bases (e.g., 24 bases for 12+12 base reads), and a long stretch of targeted nucleic acid 605 ranging in length from about 100 to about 1000 bases or more. Such constructs can be created using, e.g., methods disclosed in U.S. application Ser. No. 11/938,106, which is incorporated by reference herein. The long stretch of targeted nucleic acid 605 is useful for designing the target-specific selection oligonucleotides used in Phase II. Once structure 602 is achieved, standard library preparation continues and adaptors are inserted at the 5' and 3' ends of the library construct (note terminal adaptors 607 of library construct 606). This combination of features provides flexibility and many advantages for Phase II.

Sequencing Library Constructs (FIG. 1, Process 120)

Figure 7:
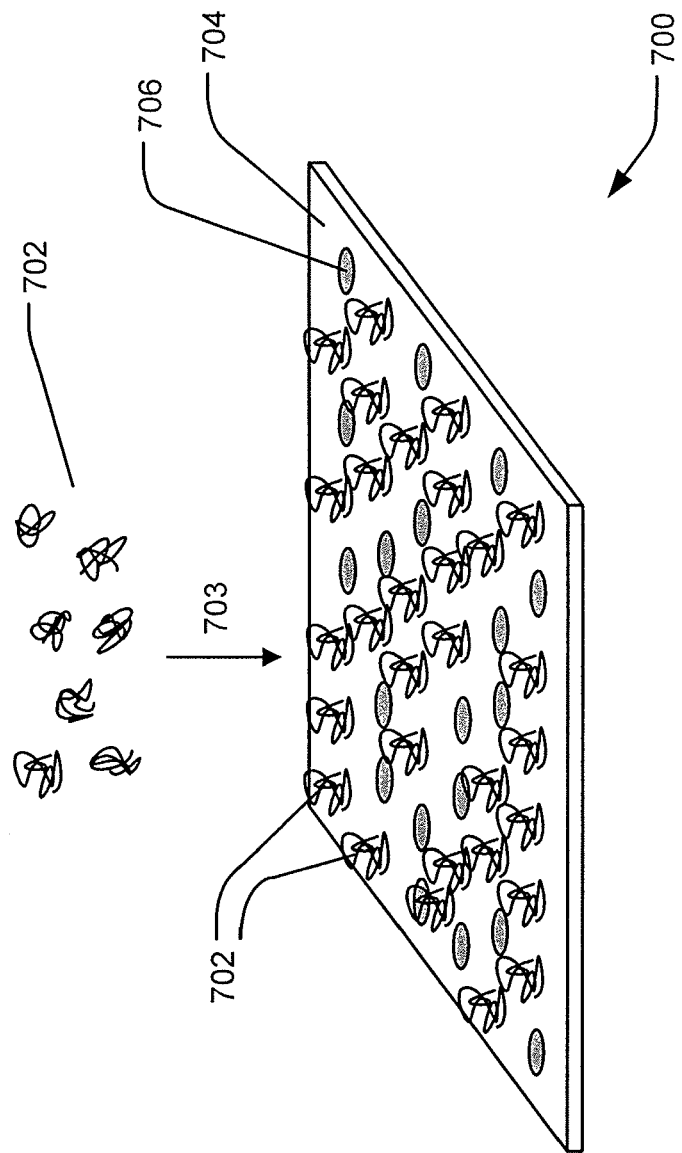
FIG. 7 is a schematic illustration of one aspect of a DNA array employing multi-adaptor nucleic acid library constructs.

FIG. 7 is a schematic illustration of one aspect of a nucleic acid array 700 employing multi-adaptor target nucleic acid library constructs. The multi-adaptor target nucleic acid library constructs in the form of DNA amplicons are seen at 702. Amplicons are arrayed on a planar matrix 704 having discrete sites 706. The amplicons 702 may be fixed to the discrete sites by a variety of techniques, including methods for covalent attachment and methods for non-covalent attachment. In one embodiment, the surface of the matrix 706 may comprise attached capture oligonucleotides that form complexes, e.g., double-stranded duplexes, with a segment of an adaptor component of the amplicon. In other, embodiments, capture oligonucleotides may comprise oligonucleotide clamps, or like structures, that form triplexes with adaptor oligonucleotides (see, e.g., U.S. Pat. No. 5,473,060). In another embodiment, the surface of the array matrix 706 may have reactive functionalities that react with complementary functionalities on the amplicons to form a covalent linkage (see, e.g., Beaucage (2001), Current Medicinal Chemistry 8:1213-1244). Once the amplicons are arrayed, the adaptors interspersed in the target nucleic acids are used to acquire sequence information of the target nucleic acids. A variety of sequencing methodologies may be used with multi-adaptor nucleic acid library constructs, including but not limited to hybridization methods as disclosed in U.S. Pat. Nos. 6,864,052; 6,309,824; 6,401,267; sequencing-by-synthesis methods as disclosed in U.S. Pat. Nos. 6,210,891; 6,828,100, 6,833,246; 6,911,345; Margulies, et al. (2005), Nature 437: 376-380 and Ronaghi, et al. (1996), Anal. Biochem. 242:84-89; and ligation-based methods as disclosed in U.S. Pat. No. 6,306,597; and Shendure et al. (2005) Science 309:1728-1739, all of which are incorporated by reference in their entirety.

In one aspect, the amplicons described herein—particularly those with inserted and interspersed adaptors—are used in sequencing by combinatorial probe-anchor ligation reaction (cPAL) (see U.S. Ser. No. 11/679,124, filed Feb. 24, 2007). In brief, cPAL comprises cycling of the following steps: First, an anchor is hybridized to a first adaptor in the amplicons (typically immediately at the 5' or 3' end of one of the adaptors). Enzymatic ligation reactions are then performed with the anchor to a fully degenerate probe population of, e.g., 8-mer probes that are labeled, e.g., with fluorescent dyes. Probes may comprise a length of about 6 to about 20 bases, or a length of about 7 to 12 bases. At any given cycle, the population of 8-mer probes that is used is structured such that the identity of one or more of its positions is correlated with the identity of the fluorophore attached to that 8-mer probe. For example, when 7-mer sequencing probes are employed, a set of fluorophore-labeled probes for identifying a base immediately adjacent to an interspersed adaptor may have the following structure: 3'-F1-NNNNNNAp, 3'-F2-NNNNNNGp. 3'-F3-NNNNNNCp and 3'-F4-NNNNNNTp (where "p" is a phosphate available for ligation). In yet another example, a set of fluorophore-labeled 7-mer probes for identifying a base three bases into a target nucleic acid from an interspersed adaptor may have the following structure: 3'-F1-NNNNANNp, 3'-F2-NNNNGNNp. 3'-F3-NNNNCNNp and 3'-F4-NNNNTNNp. To the extent that the ligase discriminates for complementarity at that queried position, the fluorescent signal provides the identity of that base.

After performing the ligation and four-color imaging, the anchor:8-mer probe complexes are stripped and a new cycle is begun. With T4 DNA ligase, accurate sequence information can be obtained as far as six bases or more from the ligation junction, allowing access to at least 12 bp per adaptor (six bases from both the 5' and 3' ends), for a total of 48 bp per 4-adaptor amplicon, 60 bp per 5-adaptor amplicon and so on.

Figure 8:
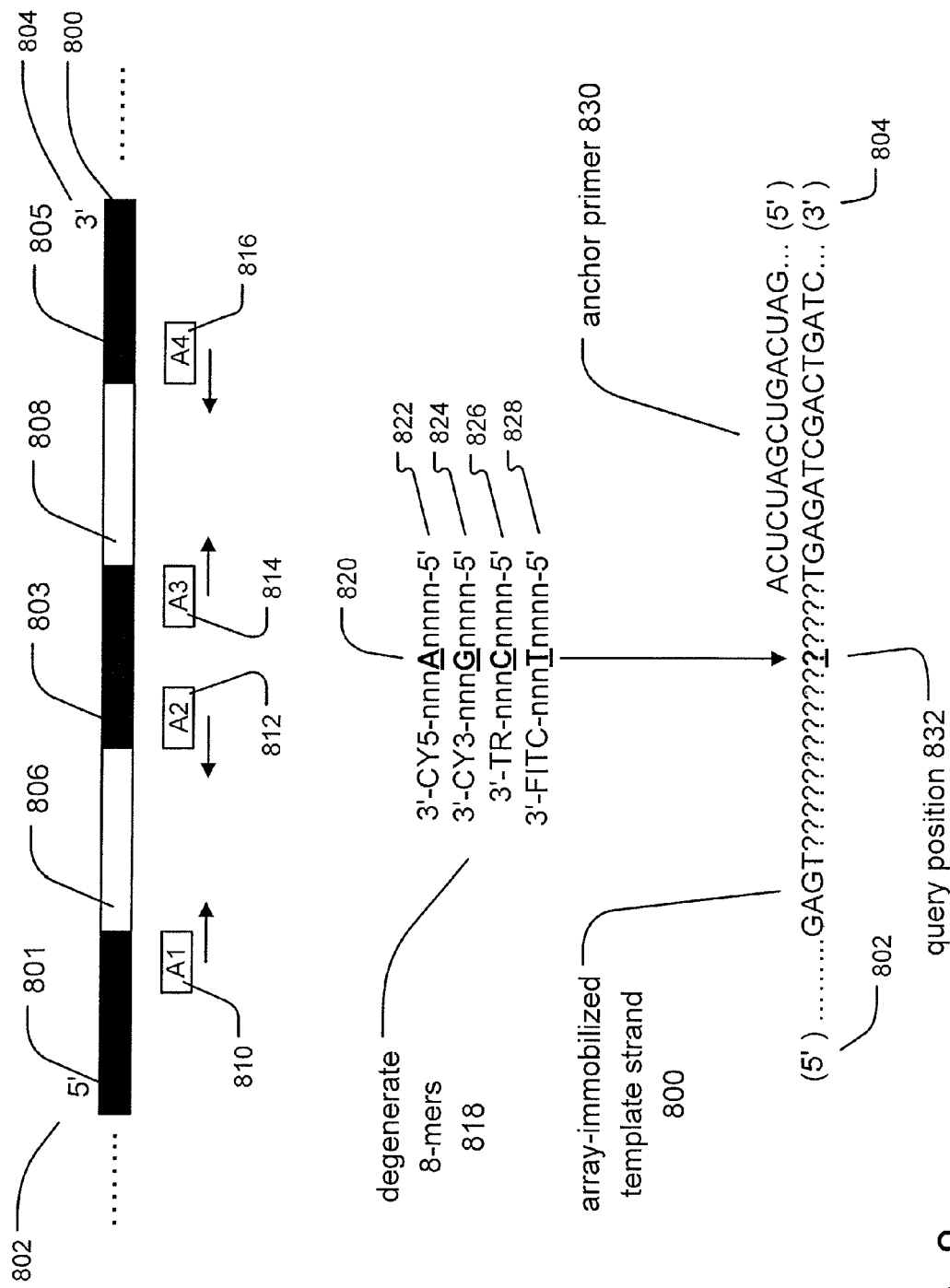
FIG. 8 is a schematic illustration of the components that may be used in an exemplary sequencing-by-ligation technique. Legend of sequences: anchor primer 830 (SEQ ID NO:1); array-immobilized template strand 800 (SEQ ID NO:2).

FIG. 8 is a schematic illustration of the components that may be used in an exemplary sequencing-by-ligation technique. A library construct 800 is shown with a stretch of target nucleic acid to be analyzed interspersed with three adaptors, with the 5' end of the stretch shown at 802 and the 3' end shown at 804. The target nucleic acid portions are shown at 806 and 808, with adaptor 1 shown at 801, adaptor 2 shown at 803 and adaptor 3 shown at 805. Four anchors are shown: anchor A1 (810), which binds to the 3' end of adaptor 1 (801) and is used to sequence the 5' end of target nucleic acid 806; anchor A2 (812), which binds to the 5' end of adaptor 2 (803) and is used to sequence the 3' end of target nucleic acid 806; anchor A3 (814), which binds to the 3' end of adaptor 2 (803) and is used to sequence the 5' end of target nucleic acid 806; and anchor A4 (816), which binds to the 5' end of adaptor 3 (805) and is used to sequence the 3' end of target nucleic acid 808.

Depending on which position that a given cycle is aiming to interrogate, the 8-mer probes are structured differently. Specifically, a single position within each 8-mer probe is correlated with the identity of the fluorophore with, which it is labeled. Additionally, the fluorophore molecule is attached to the opposite end of the 8-mer probe relative to the end targeted to the ligation junction. For example, in the graphic shown here, the anchor 830 is hybridized such that its 3' end is adjacent to the target nucleic acid. To query a position five bases into the target nucleic acid, a population of degenerate 8-mer probes shown here at 818 may be used. The query position is shown at 832. In this case, this correlates with the fifth nucleic acid from the 5' end of the 8-mer probe, which is the end of the 8-mer probe that will ligate to the anchor. In the aspect shown in FIG. 8, the 8-mer probes are individually labeled with one of four fluorophores, where Cy5 is correlated with A (822), Cy3 is correlated with G (824), Texas Red is correlated with C (826), and FITC is correlated with T (828).

Many different variations of cPAL or other sequencing-by-ligation approaches may be selected depending on various factors such as the volume of sequencing desired, the type of labels employed, the number of different adaptors used within each library construct, the number of bases being queried per cycle, how the amplicons are attached to the surface of the array, the desired speed of sequencing operations, signal detection approaches and the like. In the aspect shown in FIG. 8 and described herein, four fluorophores were used and a single base was queried per cycle. It should, however, be recognized that eight or sixteen fluorophores or more may be used per cycle, increasing the number of bases that can be identified during any one cycle. The degenerate probes (in FIG. 8, 8-mer probes) can be labeled in a variety of ways, including the direct or indirect attachment of radioactive moieties, fluorescent moieties, colorimetric moieties, chemiluminescent moieties, and the like. Many comprehensive reviews of methodologies for labeling DNA and constructing DNA adaptors provide guidance applicable to constructing oligonucleotide probes of the present invention. Such reviews include Kricka (2002), *Ann. Clin. Biochem.,* 39: 114-129; and Haugland (2006), *Handbook of Fluorescent Probes and Research Chemicals,* 10th Ed. (Invitrogen/Molecular Probes, Inc., Eugene); Keller and Manak (1993), *DNA Probes,* 2nd Ed. (Stockton Press, New York, 1993); and Eckstein (1991), Ed., *Oligonucleotides and Analogues: A Practical Approach* (IRL Press, Oxford); and the like.

In one aspect, one or more fluorescent dyes are used as labels for the oligonucleotide probes. Labeling can also be carried out with quantum dots, as disclosed in the following patents and patent publications, incorporated herein by reference: U.S. Pat. Nos. 6,322,901; 6,576,291; 6,423,551; 6,251,303; 6,319,426; 6,426,513; 6,444,143; 5,990,479; 6,207,392; 2002/0045045; 2003/0017264; and the like. Commercially available fluorescent nucleotide analogues readily incorporated into the degenerate probes include, for example, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red, the Cy fluorophores, the Alexa Fluor® fluorophores, the BODIPY® fluorophores and the like. FRET tandem fluorophores may also be used. Other suitable labels for detection oligonucleotides may include fluorescein (FAM), digoxigenin, dinitrophenol (DNP), dansyl, biotin, bromodeoxyuridine (BrdU), hexahistidine (6xHis), phosphor-amino acids (e.g. P-tyr, P-ser, P-thr) or any other suitable label.

In yet another alternative aspect, parallel sequencing of the target nucleic acids in the amplicons is performed by sequencing-by-synthesis techniques as described in U.S. Pat. Nos. 6,210,891; 6,828,100, 6,833,246; 6,911,345; Margulies, et al. (2005), *Nature* 437:376-380 and Ronaghi, et al. (1996), *Anal. Biochem.* 242:84-89. Briefly, modified pyrosequencing, in which nucleotide incorporation is detected by the release of an inorganic pyrophosphate and the generation of photons, is performed on the amplicons in the array using sequences in the adaptors for binding of the primers that are extended in the synthesis.

In an alternative aspect of the claimed invention, parallel sequencing of the target nucleic acids in the amplicons on a random array is performed by combinatorial sequencing-by-hybridization (cSBH), as disclosed by Drmanac in U.S. Pat. Nos. 6,864,052; 6,309,824; and 6,401,267. In one aspect, first and second sets of oligonucleotide probes are provided, where each set has member probes that comprise oligonucleotides having every possible sequence for the defined length of probes in the set. For example, if a set contains probes of length six, then it contains 4096 ($4^6$) probes. In another aspect, first and second sets of oligonucleotide probes comprise probes having selected nucleotide sequences designed to detect selected sets of target polynucleotides. Sequences are determined by hybridizing one probe or pool of probes, hybridizing a second probe or a second pool or probes, ligating probes that form perfectly matched duplexes on their target sequences, identifying those probes that are ligated to obtain sequence information about the target nucleic acid sequence, repeating the steps until all the probes or pools of probes have been hybridized, and determining the nucleotide sequence of the target nucleic acid from the sequence information accumulated during the hybridization and identification processes.

Imaging acquisition may be performed by methods known in the art, such as use of the commercial imaging package Metamorph. Data extraction may be performed by a series of binaries written in, e.g., C/C++, and base-calling and read-mapping may be performed by a series of Matlab and Perl scripts. As described above, for each base in a target nucleic acid to be queried (for example, for 12 bases, reading 6 bases in from both the 5' and 3' ends of each target nucleic acid portion of each amplicon), a hybridization reaction, a ligation reaction, imaging and a primer stripping reaction is performed. To determine the identity of each amplicon in an array at a given position, after performing the biological sequencing reactions, each field of view ("frame") is imaged with four different wavelengths corresponding to the four fluorescent, e.g., 8-mer probes used. All images from each cycle are saved in a cycle directory, where the number of images is 4× the number of frames (for example, if a four-fluorophore technique is employed). Cycle image data may then be saved into a directory structure organized for downstream processing.

Data extraction typically requires two types of image data: bright field images to demarcate the positions of all amplicons in the array; and sets of fluorescence images acquired during each sequencing cycle. The data extraction software identifies all objects with the brightfield images, then for each such object, computes an average fluorescence value for each sequencing cycle. For any given cycle, there are four data-points, corresponding to the four images taken at different wavelengths to query whether that base is an A, G, C or T. These raw base-calls are consolidated, yielding a discontinuous sequencing read for each amplicon. The next task is to match these sequencing reads against a reference nucleic acid sequence, e.g., a genome.

Identifying Missing or Low Confidence Sequences (FIG. 1, Process 130)

Information regarding the reference nucleic acid sequence may be stored in a reference table. A reference table may be compiled using existing sequencing data on the organism of choice. For example, human genome data can be accessed through the National Center for Biotechnology Information at ftp.ncbi.nih.gov/refseq/release, or through the J. Craig Venter Institute at http://www.jcvi.org/researchhuref/. All or a subset of human genome information can be used to create a reference table for particular sequencing queries. In addition, specific reference tables can be constructed from empirical data derived from specific populations, including genetic sequence from humans with specific ethnicities, geographic heritage, religious or culturally-defined populations, as the variation within the human genome may slant the reference data depending upon the origin of the information contained therein.

Generally, the large scale organization and local composition of nucleic acid affects the difficulty and complication of determining its sequence. Genomes of higher organisms vary considerably in their relative GC to AT content and in the number and types of repetitive elements they contain. For example, the human genome comprises genes that occur in single or few copies, multi-gene families scattered throughout the chromosomes and gene clusters in a variety of arrangements. A large proportion of the remainder of the human genome consists of various types of repetitive elements including LINEs and SINEs, of which the Alu sequences are the most widely known. Many other sequence elements are also repeated, sometimes hundreds of times.

The task that sequence assembly software must accomplish is to render a nucleic acid sequence read from the sequence data obtained and, ideally, to give, for each base, a probability that the nucleic acid sequence is correct Global sequence assembly generally can be divided into three steps: first, all possible overlaps between sequence readings are found by comparing each reading in both orientations to all other readings; second, from the list of overlapping readings, the best layout of the readings is produced; and third, from the alignment of the readings in the final layout, a consensus sequence is derived.

The first step is usually performed in two stages. First, a rapid comparison is performed to find all pairs of readings that share an exact match of, for example, fifteen consecutive bases. Second, those readings that contain these matches are aligned using dynamic programming methods. The alignments that satisfy some preset criteria are "stored" in, e.g., a graph, in which the vertices represent the readings and the edges represent the overlaps. Several different algorithms have been published that can analyze and prune these graphs to produce a consistent left-to-right ordering, orientation, and positioning for the readings. The resulting layout of the readings usually still requires multiple sequence alignments, as it is based on individual pairwise alignments, each of which may conflict with others that they overlap. Once this has been done, a consensus can be derived. Descriptions of the assembly problem and particular algorithmic solutions can be found in Kececioglu and Myers, (1995), *Algorithmica,* 13:7-51; and Myers (1995), *J. Comput. Biol.,* 2:275-90.

Sequence alignment programs also usually include a number of important and effective extra methods. For example, all readings can be prescreened to see if they contain sequences of known repeats. Those that do can be set aside or treated in other ways. For example, the segments containing repeat elements can be ignored during the search for an exact initial match, but then used during the alignment phase. The layout can be checked and altered to be consistent with known read-pair data. The quality of the alignments can be scored by using the confidence values of the bases, and these scores can be used when the overlap graph is analyzed to produce the layout. There are several widely used global assembly engines. Those that are currently available include phrap;

FAKII; CAP3 (Huang (1996), *Genomics* 33: 21.); the TIGR assembler (Sutton, et al. (1995), *Genome Sci. Technol.* 1:9-19); gap4 (Bonfield, et al. (1995), *DNA Sequence* 6:109-117); Sequencher and DNASTAR.

Using consensus algorithms, assembly databases can be used to find segments of sequence that require further readings; for example, to resolve disagreements, fulfill a pre-selected or pre-defined standard, e.g., requirement for data from both strands of the nucleic acid; or extend readings to try to join them to others and/or to fill missing sequence. The assembly databases can then be used to design the target-specific selection oligonucleotides for Phase II. After the global assembly engines have done their best with the initial shotgun sequence data, the readings are arranged into overlapping sets, and the process is completed by obtaining readings in Phase II to fill the gaps or clarify inconsistencies. At the end of the two-phase process, there is only one overlapping set of sequence readings covering the whole of the target sequence.

Defining Sequences for and Synthesizing Target-Specific Selection Oligonucleotides (FIG. 1, Processes 140 and 150)

A preferred aspect for two-phase shotgun sequencing is to integrate Phase I sequencing and sequence assembly with miniaturized and parallelized synthesis of large pools of the target-specific selection oligonucleotides that are used to select the library constructs that need to sequenced in Phase II; that is, the library constructs that comprise targeted nucleic acid sequences. In sequencing missing or low confidence readings, or in sequencing other select targeted nucleic acid sequences from a sample for Phase II, selection or enrichment of a large number of targeted nucleic acid segments in parallel—typically, from 10,000 to 100,000 or more—is required. For each targeted nucleic acid segment, at least one, and perhaps as many as about 3 to about 6 target-specific selection oligonucleotides of approximately 15-70 bases in length, or, preferably, about 25-50 bases in length, are employed. Thus, a large number of target-specific selection oligonucleotides may be required for Phase II; however, because the target-specific selection oligonucleotides can be used in a "pool" or cocktail without need for individual handling or separate reactions, the methods are not complex. Additionally, the methods provide for efficient selection of the targeted nucleic acid segments such that only minimal amounts of each target-specific selection oligonucleotide are required.

In some aspects, the 200-10,000 uninterrupted bases in the library constructs (such as those shown in FIG. 6) are used to design one or more target-specific selection oligonucleotides of, e.g., 20-30 bases in length for each of the targeted nucleic acid segment. Each target-specific selection oligonucleotide is likely to identify many overlapping fragments covering each targeted nucleic acid segments as well as sequence surrounding the targeted nucleic acid segments. For predominately small targeted regions, library constructs with shorter targeted nucleic acid segments may be used to minimize unnecessary sequencing. For predominantly large targeted nucleic acid segments, longer nucleic acid fragments typically are used in the library constructs as a single target-specific selection oligonucleotide can select targeted nucleic acid segments that cover several kilobases of sequence. For example, to select the approximately 30,000 genes in the human genome, about 50,000 oligonucleotides—each selecting 10 kb—would be sufficient to reduce the sequencing effort from 3 billion bases to 500 million bases, a 6× reduction in effort.

In various aspects, the target-specific selection oligonucleotides used in Phase II of the shotgun sequencing methods are synthesized automatically based on the assembly information from the sequence reads from the Phase I sequencing effort. Design of the target-specific selection oligonucleotides may be facilitated by the aid of a computer program such as, for example, DNAWorks (Hoover and Lubkowski (2002), *Nucleic Acids Res.* 30: e43), or Gene2Oligo (Rouillard et al. (2004), *Nucleic Acids Res.* 32: W176-180). In certain embodiments, it may be desirable to design the target-specific selection oligonucleotides to have substantially similar melting temperatures in order to facilitate manipulation of the target-specific selection oligonucleotides in a single pool. In other aspects, several pools may be employed. The process for designing target-specific selection oligonucleotides preferably is facilitated by the computer programs described above. Normalizing melting temperatures between a variety of oligonucleotide sequences may be accomplished by, e.g., varying the length of the oligonucleotides.

Target-specific selection oligonucleotides may be prepared by any method known in the art for the preparation of oligonucleotides having a desired sequence. Preferably, the target-specific selection oligonucleotides are synthesized using a method that permits high-throughput, parallel synthesis so as to reduce cost and production time and increase flexibility in the sequencing process. In one aspect, target-specific selection oligonucleotides are synthesized on a solid support in an array format, e.g., a microarray of single-stranded DNA segments synthesized in situ on a common substrate where each oligonucleotide is synthesized on a separate feature or location on the substrate. Preferably the target-specific oligonucleotides comprise inexpensive, easily-made, long, natural oligonucleotides; i.e., oligonucleotides that have no phosphorylations, modifications or labels. Such target-specific selection oligonucleotides provide high specificity and may be designed to target a uniform amount of targeted nucleic acid segments between the different adaptors. Using library constructs as described and shown in FIG. 6 provides flexibility for target-specific oligonucleotide design. Having 200-10,000 bases of targeted nucleic acid segments available for selection of one or more target-specific selection oligonucleotides that are unique in the genome (e.g., the next best binding site in the genome has multiple mismatches) or highly underrepresented in the genome (e.g., a 20-30 mer that has some or all 8-12 mers underrepresented relative to expected frequency) for the target-specific selection oligonucleotides provides flexibility for access to virtually any random base in the targeted nucleic acid segments and provides flexibility in the assay design for the Phase II sequencing.

Until recently, the high cost of making individual photolithography masks meant that methods for making high-density oligonucleotide arrays were only available for mass production of arrays and were not accessible for the individual design of single arrays. However, the application of digital micromirror devices (DMD) to array synthesis has made it much more straightforward and inexpensive to design and manufacture individual (i.e., "one off") arrays. The DMD is a chip comprising an array of micromechanical aluminum mirrors, where each mirror is individually addressable. Using the aluminum mirrors under software control to shine light in specific patterns, coupled with photo-deposition chemistry, produces arrays of oligonucleotides. Several companies and laboratories have implemented this technology, notably Xeotron and Nimblegen. For example, the Geniom one (febit, GmbH, Heidelberg, Germany) uses DMD technology to create an array by spatially-selective deprotection of photolabile protecting groups on DNA chains growing on a surface. Each new array design can be specified simply and rapidly by software with no need to make photolithography masks. The benefit of this system is that it can rapidly iterate array synthesis based on information that is obtained from the sequence assembly in Phase I. Other methods for synthesizing target-specific selection oligonucleotides include, for example, light-directed methods utilizing masks, flow channel methods, spotting methods, pin-based methods, microtube-based methods and methods utilizing multiple supports.

Methods may be devised to synthesize the target-specific selection oligonucleotides to optimize efficiency. For example, the synthesis arrays may be designed to group oligonucleotides that share a first base to be synthesized; e.g., all oligonucleotides are grouped into one of four quadrants, one for each initial base. Alternatively or in addition, pre-made arrays of all 6-mers in may be used as a basis for further synthesis of the additional 10-20 or more bases needed for the target-specific selection oligonucleotides. Such approaches may reduce synthesis time from 20 to 40%.

In some aspects, the support-bound target-specific selection oligonucleotides may be removed from the solid support prior to hybridization to the library constructs. The target-specific selection oligonucleotides may be removed from the solid support, for example, by exposure to conditions such as acids, bases, oxidation, reduction, heat, light, metal ion catalysis, displacement or elimination chemistry, or by enzymatic cleavage.

In one embodiment, target-specific selection oligonucleotides are synthesized such that they are attached to a solid support through a cleavable linkage moiety. For example, the solid support may be functionalized to provide cleavable linkers for covalent attachment to the oligonucleotides. Alternatively, the cleavable moiety may be within the target-specific selection oligonucleotides and may be introduced during in situ synthesis. A broad variety of cleavable moieties are available in the art of solid phase and microarray oligonucleotide synthesis (see, e.g., Pon, R. (1993), *Methods Mol. Biol.* 20:465-496; Verma et al. (1998), *Annu. Rev. Biochem.* 67:99-134; and U.S. Pat. Nos. 5,739,386 and 5,700,642). A suitable cleavable moiety may be selected to be compatible with the nature of the protecting group of the nucleoside bases, the choice of solid support, and/or the mode of reagent delivery, among other considerations. In an exemplary embodiment, the target-specific selection oligonucleotides, once cleaved from the solid support, contain a free 3'-OH end. Alternatively, a free 3'-OH end may be obtained by chemical or enzymatic treatment, following the cleavage of target-specific selection oligonucleotides from the support. The cleavable moiety is removed under conditions that do not degrade the target-specific selection oligonucleotides. In preferred aspects, the linker is cleaved typically by using one of two approaches; either (a) simultaneously under the same conditions as the deprotection step or (b) subsequently utilizing a different condition or reagent for linker cleavage after the completion of the deprotection step.

The covalent immobilization site may either be at the 5' end of the target-specific selection oligonucleotides, at the 3' end of the target-specific selection oligonucleotides, or within the target-specific selection oligonucleotides. In some aspects, the cleavable sites include chemically cleavable groups, such as dialkoxysilane, 3'-(S)-phosphorothioate, 5'-(S)-phosphorothioate, 3'-(N)-phosphoramidate, 5'-(N)phosphoramidate, and ribose. Synthesis and cleavage conditions of chemically cleavable oligonucleotides are described in. U.S. Pat. Nos. 5,700,642 and 5,830,655. In other aspects, a non-cleavable hydroxyl linker may be converted into a cleavable linker by coupling a special phosphoramidite to the hydroxyl group prior to the phosphoramidite or H-phosphonate oligonucleotide synthesis as described in U.S. Patent Application Publication No. 2003/0186226. The cleavage of the chemical phosphorylation agent at the completion of synthesis yields an oligonucleotide bearing a phosphate group at the 3' end. The 3'-phosphate end may be converted to a 3' hydroxyl end by treatment with a chemical or an enzyme, such as alkaline phosphatase. In yet another aspect, the cleavable linking moiety may be an amino linker which may be cleaved with 80% acetic acid yielding a 3'-phosphorylated oligonucleotide. In yet another aspect, the cleavable linking moiety may be a photocleavable linker, such as an ortho-nitrobenzyl photocleavable linker. Synthesis and cleavage conditions of photolabile oligonucleotides on solid supports are described, for example, in Venkatesan et al. (1996), *J. of Org. Chem.*, 61:525-529, Kahl et al. (1999), *J. of Org. Chem.*, 64:507-510, and U.S. Pat. No. 5,739,386. Also, target-specific selection oligonucleotides may be removed from a solid support by an enzyme such as nucleases and/or glycosylases. For example, a wide range of oligonucleotide bases, e.g., uracil, may be removed by a DNA glycosylase which cleaves the N-glycosylic bond between the base and deoxyribose, thus leaving an abasic site (Krokan et. al. (1997), *Biochem. J.* 325:1-16)). The abasic site in an oligonucleotide may then be cleaved by an AP endonuclease such as Endonuclease IV, leaving a free 3'-OH end.

Hybridization and Ligation of Library Constructs, Target-Specific Selection Oligonucleotides and Universal Oligonucleotides (FIG. 1, Processes 160 and 170)

The selection portion of Phase II of the shotgun sequencing methods described herein is based on ligation of target-specific selection oligonucleotides and universal oligonucleotides hybridized to the targeted nucleic acid segments within the library constructs. As discussed, preferably the target-specific selection oligonucleotides are about 20-30 bases in length with no modifications or phosphorylations; thus, they are easily and inexpensively made. The universal oligonucleotide set consists of probes of the following general formula: 5' P-BxNy-Tag 3', comprising a phosphorylated 5' end, 1-3 specific bases (B), about 6-12 degenerate or universal, natural or modified (e.g., LNA) bases (N), and a capture tag such as biotin at the 3' end. Examples of universal oligonucleotides include: P-CNNNNNNNNN-Biotin, P-CCNNNNNNNN-Biotin, a set of, e.g., 2-4 P-BBNNNNNNNNNNN-Biotin, a set of, e.g., 8-16 of P-BBBNNNNNNN-Biotin. When a set of universal oligonucleotides such as P-BBNNNNNNNN-Biotin is used, the set may be complete; that is, a set may comprise 16 oligonucleotides (each BB combination), or the set may comprise a subset of the 16 (e.g., selected BB combinations). The target-specific selection oligonucleotides are selected to work in concert with the sequences of universal oligonucleotides to select and capture targeted nucleic acid segments; e.g., a target-specific selection oligonucleotide would have a complementary sequence to track a targeted nucleic acid segment, but at the 3' end would end before a G in the target sequence when universal oligonucleotide P-CNNNNNNNNN-Biotin is used. This design allows the phosphorylated C of the universal oligonucleotide to hybridize to the G of the targeted nucleic acid segment.

FIG. 9 is a schematic illustration of exemplary targeted nucleic acid segments, target-specific selection oligonucleotides and universal oligonucleotides in various stages of the claimed methods. Targeted nucleic acid segment 902, target-specific selection oligonucleotide 904 and universal oligonucleotide 906 are shown, where lower case b's "b" are bases in a targeted nucleic acid segment, upper case B's "B" are specified bases in the target-specific selection oligonucleotide and the universal oligonucleotide, upper case N's "N" are degenerate or universal bases in the universal oligonucleotide, with G denoting the base in the targeted nucleic acid segment that hybridizes to the C specified base of the universal oligonucleotide. Structure 908 of FIG. 9 shows the target-specific selection oligonucleotide 904 and the universal oligonucleotide 906 hybridized to the targeted nucleic acid segment 902, while structure 910 shows the target-specific selection oligonucleotide 904 and the universal oligonucleotide 906 ligated to one another (at 912), while being hybridized to the targeted nucleic acid segment 902.

In one example, a set of eight P-BBBNNNNNNN-Biotin universal oligonucleotides are used (where a full degenerative set of three specific-base universal oligonucleotides of the formula P-BBBNNNNNN-Biotin would comprise probes); therefore, only ⅛ of all possible target-specific selection oligonucleotides in the available targeted nucleic acid segment need to be used (i.e., 50 target-specific selection oligonucleotides for a 400 bp nucleic acid segment present in the construct). The sets of universal oligonucleotides may be mixed in a pool or used in separate reactions with specific pools of target-specific selection oligonucleotides. The universal oligonucleotide-based ligation assay provides added specificity for the selection due to the ligation "proof-read," in addition to adding an additional 1 to 3 (or more) bases for sequence-specific binding to the targeted nucleic acid segments. Furthermore, the universal oligonucleotide provides functionalities such as a 5' phosphate for ligation to the target-specific oligonucleotides, as well as a capture entity such as biotin to, e.g., select and isolate to the targeted nucleic acid segment. Providing these functionalities in a "universal oligonucleotide" format obviates the need for synthesizing each target-specific selection oligonucleotide to include them; however, in some aspects, target-specific selection oligonucleotides may be designed to comprise a tag, and universal oligonucleotides (and a ligation process) are not used.

In some aspects, an optional process is used to clean up the targeted nucleic acid segment:target-specific selection oligonucleotide hybrid reaction. A "capture oligonucleotide" complementary to <one of the adaptors in the library constructs is used to capture the targeted nucleic acid segment: target-specific selection oligonucleotide hybrid to allow removal of unbound target-specific selection oligonucleotides under mismatch discriminative conditions. The capture oligonucleotide may have cleavable sites (uracil, light-cleavable bonds, restriction enzyme binding sites) for easy release of captured library constructs. The release process is performed in such a way that does not de-couple the target-specific selection oligonucleotide from the library construct. In addition, the concentration of library constructs in the reaction preferably is kept low to minimize re-hybridization of complementary target strands, especially from areas in the targeted nucleic acid segments where there are repeated sequences.

Next, universal oligonucleotides are hybridized, and, in some aspects, simultaneously or sequentially ligated to the target-specific selection oligonucleotides that are hybridized to the library constructs using ligation reagents such as T4 ligase under conditions that allow for discrimination of mismatches around the ligation site. To exploit and enhance the specificity of the ligase, the diversity of the 5' end sequences of the target-specific oligonucleotides may be widely varied by design. In some aspects, the hybridization and ligation steps are combined, whereas in other aspects the processes are performed sequentially. Because the target-specific selection oligonucleotides are not phosphorylated and the universal oligonucleotides are phosphorylated at their, e.g., 3' end and are blocked at their, e.g., 5' end by, e.g., biotin or other functional group, ligation may only take place between the 5' end of one target-specific selection oligonucleotide and the 3' end of one universal oligonucleotide. Furthermore, in some aspects, the 5' and 3' ends of the library constructs are blocked by the two arms of the last-added adaptor to prevent unwanted library construct chimeras.

In preferred aspects as described, the universal oligonucleotides are kept quite short (8-12 bases in length) such that if a universal oligonucleotide does not ligate to a target-specific selection oligonucleotide, the universal oligonucleotides melt easily from the library constructs while the target-specific selection oligonucleotides (preferably about 20-30 bases in length) do not. For example, the temperature can be optimized to between about 20°-40° C. and can be cycled in the selected range. Doing so minimizes the total amount of universal oligonucleotides needed and prevents blocking of ligation sites by other universal oligonucleotides.

To obtain a substantially uniform amount of selected library constructs for each targeted nucleic acid segment, a preferred result is to capture about 50% or more of each targeted nucleic acid segment. One approach to obtaining a uniform capture is to select target-specific selection oligonucleotides that have ΔGs similar to the universal oligonucleotides. Another approach is to provide an amount of target-specific selection oligonucleotides that is lower than the expected number of corresponding sites in the targeted nucleic acid segments to limit and equalize the amount of captured targeted nucleic acid segments. Such procedures reduce the bias that may exist if library constructs are differentially amplified before selection.

Capturing and Sequencing Targeted Nucleic Acid Segments from the Library Constructs (FIG. 1, Processes 180 and 190)

Next, in some aspects, the targeted nucleic acid segments, target-specific selection oligonucleotides (and, in one embodiment, universal oligonucleotides) are hybridized in solution and then captured on a support such as a micro- or nano-bead coated with, e.g., streptavidin. To achieve rapid reaction times with small amounts of target-specific selection oligonucleotides, a low reaction volume is preferred. A preferred way to minimize reaction volumes is to hybridize the library constructs to the target-specific selection (and universal) oligonucleotides in solution. Next, an excess of streptavidin molecules is employed to capture substantially all oligonucleotides bound to the library constructs. The strepavidin preferably is used in excess to unbound library constructs. In some aspects, these conditions are achieved by dilution of the reaction with the capturing beads (or other matrix, column or support). Furthermore, use of small beads increases the available strepavidin per surface area of the bead and is a preferred aspect.

After capturing library constructs on the beads, a careful wash is used to remove as many of the uncaptured library constructs as possible. In some aspects of the methods herein, the ligation of the target-specific selection oligonucleotides and the universal oligonucleotides is performed at this point, rather than at the time the universal oligonucleotides are hybridized to the target-specific selection oligonucleotide: targeted nucleic acid segment complex. In the capture process, many targeted nucleic acid segments will be captured by the universal oligonucleotides only. Therefore, various washing conditions are employed to disrupt these shorter (e.g., 8-12 bases in length) hybrids (i.e., the universal oligonucleotides only) and preserve the longer hybrids of 28-42 bases in length comprising the target-specific selection oligonucleotides extended by ligation with the universal oligonucleotides (i.e, 20-30+8-12). In addition, to prevent and/or disrupt library constructs from absorbing to the bead surface, the beads may be pre-incubated with unrelated nucleic acids or some other blocking agent.

After removal of molecules that are nonspecifically bound, the remaining library constructs are released under melting conditions and collected in solution for further processing. Alternatively, the universal oligonucleotides may comprise a cleavable site (e.g., uracil, light-cleavable bond, restriction enzyme binding site) for easy release of captured library constructs.

Due to the small amount of library constructs that are likely collected (0.1 to 10 ng range), a preferred next step is DNA amplification. The amplification step can be used to amplify substantially the entire library constructs, or, in some aspects, the amplification step can be used to selectively amplify the portion of the library construct between certain adaptors and to select against the other parts of the library construct; particularly the long stretch of the targeted nucleic acid segment in the library construct that was useful for designing the target-specific selection oligonucleotides. In a preferred approach, short amplicons (100-200 bases in length) are generated by PCR using primers complementary to some or all of the adaptors in the library constructs, and these amplicons are then used for forming single-stranded nucleic acid circles that are subjected to circle dependent replication (CDR) to form DNA amplicons as described previously. Once the DNA amplicons are formed and arrayed, the amplicons are sequenced by the methods described previously.

Hybridization of Library Constructs and Target-Specific Selection Oligonucleotides, Amplification by CDR and Sequencing (FIG. 1, Processes 170, 175 and 190)

In an alternative aspect to employing universal oligonucleotides and capture and release procedures, aspects of the methods employ instead hybridizing the target-specific selection oligonucleotides to the targeted nucleic acid segments in circular form (i.e., circularizing the library constructs with, e.g., Circligase), and performing circle dependent replication to form DNA amplicons that can then be arrayed and sequenced as described infra. The circle dependent replication is performed, e.g., by using the target-specific selection oligonucleotides as specific primers, and the amplification process progresses as the amplification product displaces its own tail, producing linear, tandem single-stranded copies of the library constructs. Once the DNA amplicons are formed and arrayed, the amplicons are sequenced by the methods described previously.

The following filed patent applications provide additional information on various processes to select for orientation of adaptors in respect to one another and methods for enriching for adaptors added in specific orientations: U.S. Ser. No. 60/864,992 filed Nov. 9, 2006; U.S. Ser. No. 11/943,703, filed Nov. 2, 2007; U.S. Ser. No. 11/943,697, filed Nov. 2, 2007; U.S. Ser. No. 11/943,695, filed Nov. 2, 2007; 60/985,441, filed Nov. 5, 2007; 60/985,753, filed Nov. 6, 2007 and PCT/US07/835,540; filed Nov. 2, 2007, all of which are incorporated by reference in their entirety.

The present specification provides a complete description of the methodologies, systems and/or structures and uses thereof in example aspects of the presently-described technology. Although various aspects of this technology have been described above with a certain degree of particularity, or with reference to one or more individual aspects, those skilled in the art could make numerous alterations to the disclosed aspects without departing from the spirit or scope of the technology hereof. Since many aspects can be made without departing from the spirit and scope of the presently described technology, the appropriate scope resides in the claims hereinafter appended. Other aspects are therefore contemplated. Furthermore, it should be understood that any operations may be performed in any order, unless explicitly claimed otherwise or a specific order is inherently necessitated by the claim language. It is intended that all matter contained in the above description and shown in the accompanying drawings shall be interpreted as illustrative only of particular aspects and are not limiting to the embodiments shown. Changes in detail or structure may be made without departing from the basic elements of the present technology as defined in the following claims. In the claims of any corresponding utility application, unless the term "means" is used, none of the features or elements recited therein should be construed as means-plus-function limitations pursuant to 35 U.S.C. §112, ¶6.

SEQUENCE LISTING

```
<160> NUMBER OF SEQ ID NOS: 2

<210> SEQ ID NO 1
<211> LENGTH: 15
<212> TYPE: RNA
<213> ORGANISM: Artificial sequence
<220> FEATURE:
<223> OTHER INFORMATION: Synthetic polynucleotide

<400> SEQUENCE: 1
gaucagucga ucuca                                                    15

<210> SEQ ID NO 2
<211> LENGTH: 15
<212> TYPE: DNA
<213> ORGANISM: Artificial sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: Residue t modified at 5' end with nucleotide of
      indeterminant length which in turn is modified at the 5' end with
      gagt

<400> SEQUENCE: 2
tgagatcgac tgatc                                                    15
```

What is claimed is:

1. A method for sequencing a target nucleic acid comprising:
    (a) sequencing the target nucleic acid to produce primary sequence information for the target nucleic acid;
    (b) identifying missing sequences and/or low confidence sequences in the target nucleic acid from the primary sequence information determined in step (a);
    (c) synthesizing a plurality of target-specific oligonucleotides,
    each corresponding to a sequence identified in step (b);
    (d) hybridizing said plurality of target-specific oligonucleotides to a library of fragments of the target nucleic acid;
    (e) hybridizing universal oligonucleotides to the library of fragments;
    (f) ligating the universal oligonucleotides that have hybridized to the target nucleic acids to adjacently hybridized target-specific oligonucleotides, thereby producing universal oligonucleotide:target-specific oligonucleotide ligation products; and
    (g) preparing an enriched library of fragments of the target nucleic acid by capturing fragments of the target nucleic acid from the library that are hybridized to the universal oligonucleotide:target-specific oligonucleotide ligation products.

2. The method of claim 1, further comprising:
    (h) sequencing fragments from the enriched library prepared in step (g); and
    (i) assembling sequence information from the fragments sequenced in step (h) with the primary sequence information determined in step (a) to produce an assembled sequence.

3. The method of claim 2, further comprising:
    (j) identifying missing sequences and/or low confidence sequences in the target nucleic acid from the sequence assembled in step (i);
    (k) synthesizing a plurality of target-specific oligonucleotides, each corresponding to a sequence identified in step (j);
    (l) performing steps (d) to (i) using the target-specific oligonucleotides prepared in step (k);
    (m) optionally repeating steps (j) to (l).

4. The method of claim 1, wherein the universal oligonucleotides comprise 5 to 15 consecutive universal bases.

5. The method of claim 4, wherein the universal oligonucleotides further comprise 1 to 5 sequence-specific bases.

6. The method of claim 1, wherein the universal oligonucleotides comprise 5 to 15 consecutive degenerate bases.

7. The method of claim 6, wherein the universal oligonucleotides further comprise 1 to 5 sequence-specific bases.

8. The method of claim 1, wherein the universal oligonucleotides comprise a capture tag.

9. The method of claim 8, wherein the capture tag is biotin.

10. The method of claim 8, wherein the universal oligonucleotide is phosphorylated at the 5' end.

11. The method of claim 1, wherein the universal oligonucleotides comprise a formula 5'-$B_x$—$N_y$-Tag-3', where B denotes a sequence specific base, x is 1 to 5, N denotes a degenerate or universal base, y is 5 to 15, and Tag is a capture tag.

12. The method of claim 1, wherein the target specific oligonucleotides are 20 to 30 bases in length.

13. The method of claim 1, wherein the hybridizing and ligating are conducted under conditions such that universal oligonucleotides not ligated to target-specific oligonucleotides melt easily from the library constructs whereas the target-specific selection oligonucleotides do not.

14. The method of claim 1, wherein step (b) comprises identifying a sequence that is missing from the primary sequence information obtained in step (a).

15. The method of claim 1, wherein step (b) comprises identifying a sequence that comprises low confidence sequences in the primary sequence information obtained in step (a).

16. The method of claim 1, wherein step (b) comprises identifying a sequence that comprises low confidence base calls in the primary sequence information obtained in step (a).

17. The method of claim 1, wherein step (b) comprises identifying missing sequences, or low confidence sequence reads by comparing the primary sequence information with a reference sequence.

18. The method of claim 1, wherein the library of fragments in step (c) is a library of DNA amplicons, each amplicon comprising multiple copies of a fragment of the target nucleic acid.

19. A method for sequencing a target nucleic acid, comprising:
(a) obtaining nucleotide sequence information for at least a portion of the target nucleic acid;
(b) identifying missing sequences and/or low confidence sequences in the nucleotide sequence information;
(c) synthesizing a plurality of target-specific oligonucleotides, each corresponding to a sequence identified in step (b);
(d) hybridizing said plurality of target-specific oligonucleotides to a library of fragments of the target nucleic acid;
(e) hybridizing universal oligonucleotides to the library of fragments;
(f) ligating the universal oligonucleotides that have hybridized to the target nucleic acids to adjacently hybridized target-specific oligonucleotides, thereby producing universal oligonucleotide:target-specific oligonucleotide ligation products;
(g) preparing an enriched library of fragments of the target nucleic acid by selecting fragments of the target nucleic acid from the library that are hybridized to the universal oligonucleotide:target-specific oligonucleotide ligation products;
(h) sequencing fragments in the enriched library; and
(i) assembling sequence information determined in step (h) with the sequence information obtained in step (a), thereby obtaining more complete sequence information.

20. The method of claim 19, further comprising:
(j) identifying missing sequences and/or low confidence sequences in the target nucleic acid from the sequence assembled in step (i);
(k) synthesizing a plurality of target-specific oligonucleotides, each corresponding to a sequence identified in step (j);
(l) performing steps (d) to (i) using the target-specific oligonucleotides prepared in step (k);
(m) optionally repeating steps (j) to (l).

21. The method of claim 19, wherein the universal oligonucleotides comprise a plurality of universal and/or degenerate bases and 1 to 5 sequence-specific bases.

22. The method of claim 19, wherein the universal oligonucleotides comprise a capture tag.

23. The method of claim 19, wherein the hybridizing and ligating are conducted under conditions such that universal oligonucleotides not ligated to target-specific oligonucleotides melt easily from the library constructs whereas the target-specific selection oligonucleotides do not.

24. The method of claim 19, wherein the library of fragments in step (c) is a library of DNA amplicons, each amplicon comprising multiple copies of a fragment of the target nucleic acid.

25. A computer controlled apparatus configured and programmed for sequencing a genome of a human organism according to a method that comprises the following steps:
(a) obtaining nucleotide sequence information for at least a portion of the genome;
(b) identifying missing sequences and/or low confidence sequences in the nucleotide sequence information;
(c) synthesizing a plurality of target-specific oligonucleotides, each corresponding to a sequence identified in step (b);
(d) hybridizing said plurality of target-specific oligonucleotides to a library of fragments of the genome;
(e) hybridizing universal oligonucleotides to the library of fragments;
(f) ligating the universal oligonucleotides that have hybridized to the target nucleic acids to adjacently hybridized sequence-specific oligonucleotides, thereby producing universal oligonucleotide:sequence-specific oligonucleotide ligation products;
(g) preparing an enriched library of fragments of the genome by capturing fragments of the genome nucleic acid from the library that are hybridized to the universal oligonucleotide:sequence-specific oligonucleotide ligation products;
(h) sequencing fragments in the enriched library; and
(i) assembling sequence information determined in step (h) with the primary sequence information obtained from step (a).

* * * * *